US011104637B2

(12) United States Patent
Parvulescu et al.

(10) Patent No.: US 11,104,637 B2
(45) Date of Patent: Aug. 31, 2021

(54) PROCESS FOR THE CONVERSION OF MONOETHANOLAMINE TO ETHYLENEDIAMINE EMPLOYING A COPPER-MODIFIED ZEOLITE OF THE MOR FRAMEWORK STRUCTURE

(71) Applicant: BASF SE, Ludwigschafen am Rhein (DE)

(72) Inventors: Andrei-Nicolae Parvulescu, Ludwigschafen am Rhein (DE); Alvaro Gordillo, Heidelberg (DE); Marie Katrin Schroeter, Ludwigschafen am Rhein (DE); Johann-Peter Melder, Ludwigschafen am Rhein (DE); Juergen Bechtel, Heidelberg (DE); Thomas Heidemann, Ludwigschafen am Rhein (DE); Stephan A. Schunk, Heidelberg (DE); Ulrich Müller, Ludwigschafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/464,894

(22) PCT Filed: Nov. 29, 2017

(86) PCT No.: PCT/EP2017/080810
§ 371 (c)(1),
(2) Date: May 29, 2019

(87) PCT Pub. No.: WO2018/099964
PCT Pub. Date: Jun. 7, 2018

(65) Prior Publication Data
US 2019/0389794 A1 Dec. 26, 2019

(30) Foreign Application Priority Data

Nov. 30, 2016 (EP) ..................... 16201339

(51) Int. Cl.
| | |
|---|---|
| *C07C 209/16* | (2006.01) |
| *B01J 29/24* | (2006.01) |
| *B01J 37/08* | (2006.01) |
| *B01J 37/30* | (2006.01) |
| *C01B 39/06* | (2006.01) |
| *C01B 39/26* | (2006.01) |

(52) U.S. Cl.
CPC ............ *C07C 209/16* (2013.01); *B01J 29/24* (2013.01); *B01J 37/08* (2013.01); *B01J 37/30* (2013.01); *C01B 39/06* (2013.01); *C01B 39/265* (2013.01); *B01J 2229/183* (2013.01)

(58) Field of Classification Search
CPC ... C07C 209/16; C07C 211/10; C07C 211/14; C01P 2002/72; B01J 29/185; B01J 37/08; B01J 2229/186; B01J 37/30; C01B 39/265; C01B 39/026; C01B 39/04; C01B 39/06
See application file for complete search history.

(56) References Cited

U.S. PATENT DOCUMENTS

| | | | | |
|---|---|---|---|---|
| 4,918,233 A | * | 4/1990 | Deeba | C07C 209/16 564/479 |
| 4,939,301 A | | 7/1990 | Grice et al. | |
| 5,235,107 A | * | 8/1993 | Shimasaki | C07C 209/60 564/487 |
| 7,405,327 B2 | * | 7/2008 | Haese | C07C 209/16 564/446 |
| 7,605,295 B1 | * | 10/2009 | Lafyatis | C07C 6/126 585/475 |
| 7,687,423 B2 | * | 3/2010 | Moscoso | B01J 29/005 502/60 |
| 7,696,384 B2 | * | 4/2010 | Cauwenberge | C07D 295/13 564/463 |
| 7,700,806 B2 | * | 4/2010 | van Cauwenberge | C07C 209/16 564/480 |

(Continued)

FOREIGN PATENT DOCUMENTS

| | | | |
|---|---|---|---|
| CN | 1962058 A | * | 5/2007 |
| CN | 101215239 A | | 7/2008 |

(Continued)

OTHER PUBLICATIONS

English-Language Machine Translation CN 100546717 (2007) (Year: 2007).*
English-Language Machine Translation CN 101406845 (2009) (Year: 2009).*
English-Language Machine Translation JP 3111622 (2000) (Year: 2000).*
English-Language Machine Translation JP 3511666 (2004) (Year: 2004).*
K. Segawa et al., Applied Catalysis A: General, 309-317 (2000) (Year: 2000).*
K. Segawa et al., Studies in 83 Surface Science Catalysts, 273-278 (1994) (Year: 1994).*
K. Segawa et al., Studies in 101 Surface Science Catalysts, 267-276 (1996) (Year: 1996).*

(Continued)

*Primary Examiner* — Alexander R Pagano
(74) *Attorney, Agent, or Firm* — Faegre Drinker Biddle & Reath LLP

(57) ABSTRACT

The present invention relates to a process for the conversion of 2-aminoethanol to ethane-1,2-diamine and/or linear polyethylenimines of the formula $H_2N-[CH_2CH_2NH]_n-CH_2CH_2NH_2$ wherein $n \geq 1$ comprising: (i) providing a catalyst comprising a zeolitic material having the MOR framework structure comprising $YO_2$ and $X_2O_3$, wherein Y is a tetravalent element and X is a trivalent element, said zeolitic material containing copper as extra-framework ions; (ii) providing a gas stream comprising 2-aminoethanol and ammonia; (iii) contacting the catalyst provided in (i) with the gas stream provided in (ii) for converting 2-aminoethanol to ethane-1,2-diamine and/or linear polyethylenimines.

13 Claims, 1 Drawing Sheet

(56) References Cited

U.S. PATENT DOCUMENTS

| | | | | |
|---|---|---|---|---|
| 8,466,080 | B2* | 6/2013 | Boldingh | C07C 6/06 |
| | | | | 502/67 |
| 8,697,834 | B2* | 4/2014 | Schaub | C07C 209/16 |
| | | | | 528/398 |
| 8,772,548 | B2* | 7/2014 | Magerlein | C07C 209/26 |
| | | | | 564/473 |
| 8,951,498 | B2* | 2/2015 | Larsen | B82Y 30/00 |
| | | | | 423/702 |
| 9,695,099 | B2 | 7/2017 | Liu et al. | |
| 2007/0232833 | A1* | 10/2007 | Haese | C07C 209/16 |
| | | | | 564/472 |
| 2011/0294977 | A1* | 12/2011 | Schaub | C08G 73/0213 |
| | | | | 528/422 |
| 2012/0271068 | A1* | 10/2012 | Magerlein | C07C 215/08 |
| | | | | 564/473 |
| 2014/0309460 | A1* | 10/2014 | Strautmann | C07C 209/16 |
| | | | | 564/480 |
| 2016/0152541 | A1 | 6/2016 | Liu et al. | |
| 2017/0128916 | A1 | 5/2017 | Lejkowski et al. | |
| 2017/0362164 | A1 | 12/2017 | Wigbers et al. | |
| 2018/0022611 | A1 | 1/2018 | Feyen et al. | |
| 2018/0036723 | A1 | 2/2018 | Riedel et al. | |
| 2018/0071679 | A1 | 3/2018 | Karpov et al. | |
| 2018/0170850 | A1 | 6/2018 | Vautravers et al. | |
| 2018/0208532 | A1 | 7/2018 | Parvulescu et al. | |
| 2018/0208533 | A1 | 7/2018 | Rudenauer et al. | |
| 2018/0215724 | A1 | 8/2018 | Gordillo et al. | |
| 2018/0243691 | A1 | 8/2018 | Mueller et al. | |
| 2018/0319758 | A1 | 11/2018 | Gordillo et al. | |
| 2018/0319759 | A1 | 11/2018 | Gordillo et al. | |
| 2018/0328601 | A1 | 11/2018 | Weickert et al. | |
| 2018/0333696 | A1 | 11/2018 | Burckhart et al. | |
| 2018/0345245 | A1 | 12/2018 | Maurer et al. | |
| 2018/0362351 | A1 | 12/2018 | Parvulescu et al. | |
| 2018/0362353 | A1 | 12/2018 | Vautravers et al. | |
| 2018/0362357 | A1 | 12/2018 | Feyen et al. | |
| 2019/0077779 | A1 | 3/2019 | Riedel et al. | |
| 2019/0134564 | A1 | 5/2019 | Feyen et al. | |
| 2019/0143272 | A1 | 5/2019 | Trukhan et al. | |
| 2019/0144290 | A1 | 5/2019 | Marx et al. | |
| 2019/0169037 | A1 | 6/2019 | Trukhan et al. | |
| 2019/0169112 | A1 | 6/2019 | Eidamshaus et al. | |
| 2019/0169149 | A1 | 6/2019 | Teles et al. | |
| 2019/0210989 | A1 | 7/2019 | Teles et al. | |
| 2019/0308928 | A1* | 10/2019 | Parvulescu | C07C 209/16 |
| 2019/0308929 | A1* | 10/2019 | Parvulescu | C07C 209/16 |
| 2019/0389794 | A1* | 12/2019 | Parvulescu | C07C 209/16 |
| 2020/0087246 | A1* | 3/2020 | Gordillo | B01J 29/405 |

FOREIGN PATENT DOCUMENTS

| | | | |
|---|---|---|---|
| CN | 101406845 A | * | 4/2009 |
| CN | 102190588 A | | 9/2011 |
| CN | 102233272 A | | 11/2011 |
| CN | 101406845 B | | 2/2012 |
| CN | 102974393 A | | 3/2013 |
| CN | 103007984 A | | 4/2013 |
| CN | 105503613 A | * | 4/2016 |
| DE | 102005047464 A1 | | 4/2007 |
| EP | 0252424 A2 | | 1/1988 |
| JP | H0687797 A | | 3/1994 |
| JP | H07247245 A | | 9/1995 |
| JP | 3111622 B2 | * | 11/2000 |
| WO | WO-2009083580 A1 | | 7/2009 |
| WO | WO-2014135662 A1 | | 9/2014 |
| WO | WO-2016096990 A1 | | 6/2016 |
| WO | WO-2016116406 A1 | | 7/2016 |
| WO | WO-2016135133 A1 | | 9/2016 |
| WO | WO-2016180807 A1 | | 11/2016 |
| WO | WO-2016180809 A1 | | 11/2016 |
| WO | WO-2017025593 A1 | | 2/2017 |
| WO | WO-2017076947 A1 | | 5/2017 |
| WO | WO-2017167622 A1 | | 10/2017 |
| WO | WO-2017211236 A1 | | 12/2017 |
| WO | WO-2017220391 A1 | | 12/2017 |
| WO | WO-2018007207 A1 | | 1/2018 |
| WO | WO-2018011280 A1 | | 1/2018 |
| WO | WO-2018015434 A1 | | 1/2018 |
| WO | WO-2018046323 A1 | | 3/2018 |
| WO | WO-2018046481 A1 | | 3/2018 |
| WO | WO-2018054740 A1 | | 3/2018 |
| WO | WO-2018054759 A1 | | 3/2018 |
| WO | WO-2018059316 A1 | | 4/2018 |
| WO | WO-2018069209 A1 | | 4/2018 |
| WO | WO-2018073292 A1 | | 4/2018 |
| WO | WO-2018073367 A1 | | 4/2018 |
| WO | WO-2018091342 A1 | | 5/2018 |
| WO | WO-2018096171 A1 | | 5/2018 |
| WO | WO-2018099966 A1 | | 6/2018 |
| WO | WO-2018099967 A1 | | 6/2018 |

OTHER PUBLICATIONS

Y. Zhang et al., 8 Catalysis Communications, 1102-1106 (2007) (Year: 2007).*
English-Language Machine Translation CN 105503613 (2016) (Year: 2016).*
CAS Abstract CN 105503613 (2016) (Year: 2016).*
Z. Wang et al., 57 Microporous and Mesoporous Materials, 1-7 (2003) (Year: 2003).*
Ch. Baerlocheretal., Atlas of Zeolite Framework Types (5th ed., 2001) (Year: 2001).*
F. Zhao et al., Industrial Catalysis, 1-11 (2008) (English-language translation) (Year: 2008).*
F. Zhao et al., 16 Industrial Catalysis, 70-72 (2008) (Year: 2008).*
Fischer, A., "Heterogeneous transition metal catalyzed amination of aliphatic diols", Doctoral Dissertation, Universität Karlsruhe (TH), Karlsruhe, Baden-Württemberg, Germany, 1998.
Grundner, S., et al., "Single-site trinuclear copper oxygen clusters in mordenite for selective conversion of methane to methanol", Nature Communications, vol. 6, Article No. 7546, (2015).
International Preliminary Examination Report for PCT/EP2017/080810 dated Nov. 20, 2018.
International Preliminary Report on Patentability for PCT/EP2017/080810 dated Jan. 15, 2018.
International Preliminary Report on Patentability for PCT/EP2017/080813 dated Jan. 30, 2018.
International Preliminary Report on Patentability for PCT/EP2017/080816 dated Jan. 8, 2018.

\* cited by examiner

PROCESS FOR THE CONVERSION OF MONOETHANOLAMINE TO ETHYLENEDIAMINE EMPLOYING A COPPER-MODIFIED ZEOLITE OF THE MOR FRAMEWORK STRUCTURE

CROSS-REFERENCE TO RELATED APPLICATIONS

This application is a national stage application (under 35 U.S.C. § 371) of PCT/EP2017/080810, filed Nov. 29, 2017, which claims benefit of European Application No. 16201339.5, filed Nov. 30, 2016.

TECHNICAL FIELD

The present invention relates to a process for the conversion of 2-aminoethanol to ethane-1,2-diamine and/or linear polyethylenimines of the formula $H_2N-[CH_2CH_2NH]_n-CH_2CH_2NH_2$ wherein n≥1, said process employing a zeolitic material having the MOR framework structure comprising $YO_2$ and $X_2O_3$, wherein Y is a tetravalent element and X is a trivalent element, said zeolitic material containing copper as extra-framework ions.

INTRODUCTION

Mordenite (MOR) zeolites are a class of large pore zeolites with 1 dimensional 12 membered ring (MR) channels and intersecting 8-MR channels (side pockets). Al substitution into the neutral silicate framework creates a charge imbalance compensated by cations (e.g., O—H group that act as Brønsted acids). These class of zeolites was previously described for various types of chemical transformations like Friedel-Crafts type reactions, isomerization, carbonilation and amination processes. The MOR zeolites synthesis was also described following different reaction pathways like template free-synthesis (in the absence of an organic pore forming agent), templated synthesis or post-modification like de-alumination reaction. Thus, WO 2014/135662 A relates to the carbonilation of dimethyl ether (DME) with syngas to methylacetate, wherein the MOR zeolite employed is preferably made with a tetraethylammonium bromide (TEABr) template. U.S. Pat. No. 7,605,295 concerns a transalkylation process employing small crystal MOR zeolites with a mean crystallite length parallel to the direction of 12 MR pores of preferably 50 nm, wherein the zeolite is made with a TEABr template. Similarly, U.S. Pat. No. 7,687,423 B2 relates to the synthesis of crystallites having the MOR framework structure with a mean crystallite length parallel to the direction of the 12-ring channels of 60 nm or less as well as to their use in the transalkylation of aromatics. Grundner, Sebastian et al. in Nat. Commun. 2015, Vol. 6, article number 7546 concerns Cu-MOR as selective/active catalyst for methane oxidation to methanol involving a specific Cu ion exchange method starting from $Cu(OAc)_2$ without consecutive calcination.

Mordenite based catalysts are also known for the synthesis of ethylene amines by gas-phase amination mainly of monoethanol amine. Thus, U.S. Pat. No. 4,918,233 reports on the use of a rare-earth doped MOR for the monoethanol amine (MEOA) gas-phase amination with 80% selectivity to EDA at 26% MEOA conversion. CN 1962058 A relates to the gas-phase synthesis of ethylene-diamine the amination of ethanolamine using a Mordenite catalyst containing one of Zr, Nb, Mo, or Sn in combination with Zn or Fe. JP H0687797 A and JP H07247245 A respectively relate to a process for the gas-phase reaction of ammonia and monothanolamine to ethylenediamine with the use of a dealuminated Mordenite catalyst. Modification of the mordenite zeolite with P for production of EDA and piperazine derivates from MEOA is also described in CN 101215239 B. CN 101406845 A describes an H-mordenite amination catalyst and its preparation. CN 102974393 A relates to a method for regeneration of modified zeolite molecular sieve amination catalysts. CN 103007984 A claims a method for manufacturing amination catalysts. CN102233272A and CN102190588A a process for preparing EDA through catalytic amination of monoethylene glycol (MEG).

In addition to these, the inaugural thesis "Heterogeneous Transition Metal Catalyzed Amination of Aliphatic Diols" from Achim Fischer, Diss. ETH No 12978, 1998, discusses zeolite catalyzed processes for the conversion of monoethyleneglycol and monoethanolamine to ethylenedia-mine, respectively. WO 2009/083580 A1 relates to a process for the production of ethylene amines from the amination of ethylene oxide, ethylene glycol, or ethanolamine using a sulfonated tetrafluoroethylene based fluoropolymer-copolymer (Nafion) as a catalyst. U.S. Pat. No. 4,918,233 concerns the production of ethylenediamine from monoethanolamine and ammonia with the use of a dealuminated Mordenite catalyst. It is noted that all of the aforementioned processes concern amination processes which are conducted in the liquid phase and require the use of high pressure.

DE 10 2005 047464 A1 discloses a process for producing ethyleneamines from reacting monoethanolamin with ammonia in the presence of a $Cu/Co/Ni/gamma-Al_2O_3$ heterogeneous catalyst.

Finally, CN 101215239 A concerns the joint preparation of ethylene diamine and aminoethyl piperazine, wherein the process involves the use of a phosphorous modified mordenite catalyst.

Despite the available methods for the amination of monoethanolamine, there remains a need for the provision of improved processes employing catalysts which not only display a higher activity but also allow for an increased selectivity with respect to the amination products, and in particular with respect to ethylene diamine.

DETAILED DESCRIPTION

It was therefore the object of the present invention to provide a process for the conversion of 2-aminoethanol to ethane-1,2-diamine and/or linear polyethylenimines of the formula $H_2N-[CH_2CH_2NH]_n-CH_2CH_2NH_2$ wherein n≥1 permitting to obtain higher yields of ethane-1,2-diamine and/or linear polyethylenimines of the formula $H_2N-[CH_2CH_2NH]_n-CH_2CH_2NH_2$ wherein n≥1, at higher conversion rates of the monoethanolamine precursor compound. Thus, it has surprisingly found that by using a catalyst comprising a zeolitic material having the MOR frame-work structure, wherein said zeolitic material containing copper as extra-framework ions, a process for the conversion of 2-aminoethanol to ethane-1,2-diamine and/or linear polyethylenimines of the formula $H_2N-[CH_2CH_2NH]_n-CH_2CH_2NH_2$ wherein n≥1 is provided permitting not only to achieve higher conversion rates, but which is furthermore more selective towards ethane-1,2-diamine and/or the aforementioned linear polyethylenimines.

Therefore, the present invention relates to a process for the conversion of 2-aminoethanol to ethane-1,2-diamine and/or linear polyethylenimines of the formula $H_2N-[CH_2CH_2NH]_n-CH_2CH_2NH_2$ wherein n≥1 comprising (i) providing a catalyst comprising a zeolitic material having the MOR framework structure comprising $YO_2$ and $X_2O_3$, wherein Y is a tetravalent element and X is a trivalent element, said zeolitic material containing copper as extra-framework ions;

(ii) providing a gas stream comprising 2-aminoethanol and ammonia;

(iii) contacting the catalyst provided in (i) with the gas stream provided in (ii) for converting 2-aminoethanol to ethane-1,2-diamine and/or linear polyethylenimines, wherein n preferably ranges from 1 to 8, more preferably from 1-5, more preferably from 1-4, more preferably from 1-3, more preferably from 1-2, wherein more preferably n=1.

Within the meaning of the present invention, the term "extra-framework ions" designates ions which are located at the ion exchange sites of the zeolitic material and thus serve to compensate the charge of the zeolitic framework, wherein according to a preferred meaning of the present invention the term "extra-framework ions" designates cations which are located at the ion exchange sites of the zeolitic material and thus serve to compensate the negative charge of the zeolitic framework.

According to the present invention, there is no particular restriction as to the amount of 2-aminoethanol in the gas stream provided in (ii) and contacted with the catalyst in (iii). Thus, by way of example, the gas stream provided in (ii) and contacted with the catalyst in (iii) may contain 2-aminoethanol in an amount in the range of from 0.1 to 10 vol.-%, preferably from 0.5 to 5 vol.-%, more preferably from 1 to 4.5 vol.-%, more preferably from 1.5 to 4 vol.-%, more preferably from 2 to 3.7 vol.-%, more preferably from 2.5 to 3.5 vol.-%, and more preferably from 2.7 to 3.3 vol.-%. It is, however, particularly preferred according to the present invention that the gas stream provided in (ii) and contacted with the catalyst in (iii) contains 2-aminoethanol in an amount in the range of from 2.9 to 3.1 vol.-%.

According to the present invention, there is in principle no restriction as to the ammonia:2-aminoethanol molar ratio in the gas stream provided in (ii) and contacted with the catalyst in (iii), provided that said molar ratio is in the range of from 1 to 45. Thus, by way of example, the ammonia:2-aminoethanol molar ratio in the gas stream provided in (ii) and contacted with the catalyst in (iii) may be in the range of from 2 to 35, preferably from 4 to 30, more preferably from 6 to 25, more preferably from 8 to 20, and more preferably from 10 to 16. It is, however, particularly preferred according to the present invention that the ammonia: 2-aminoethanol molar ratio in the gas stream provided in (ii) and contacted with the catalyst in (iii) is in the range of from 12 to 14.

As regards the ammonia content in the gas stream provided in (ii) and contacted with the catalyst in (iii), no particular restrictions apply such that any conceivable amount of ammonia may be chosen for conducting the process of the present invention. Thus, by way of example, the amount of ammonia in the gas stream provided in (ii) and contacted with the catalyst in (iii) may be in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%. It is, however, particularly preferred according to the present invention that the gas stream provided in (ii) and contacted with the catalyst in (iii) contains ammonia in an amount in the range of from 39 to 41 vol.-%.

According to the present invention, there is in principle no restriction as to the content of hydrogen in the gas stream provided in (ii) and contacted with the catalyst in (iii). Thus, by way of example, the gas stream provided in (ii) and contacted with the catalyst in (iii) may contain 1 vol.-% or less of hydrogen, preferably 0.5 vol.-% or less, more preferably 0.1 vol.-% or less, more preferably 0.05 vol.-% or less, more preferably 0.001 vol.-% or less, and more preferably 0.0005 vol.-% or less. It is, however, particularly preferred according to the present invention that the gas stream provided in (ii) and contacted with the catalyst in (iii) contains 0.0001 vol.-% or less of hydrogen.

Alternatively, by way of example, the gas stream provided in (ii) and contacted with the catalyst in (iii) may further contain hydrogen in an amount in the range of from 0.1 to 70 vol.-%, preferably from 0.5 to 50 vol.-%, more preferably from 1 to 40 vol.-%, more preferably from 5 to 35 vol.-%, more preferably from 10 to 30 vol.-%, more preferably from 15 to 25 vol.-%, more preferably from 17 to 23 vol.-%. It is, however, particularly preferred according to the present invention that the gas stream provided in (ii) and contacted with the catalyst in (iii) contains from 19 to 21 vol.-% of hydrogen.

According to the present invention, it is preferred that the gas stream provided in (ii) and contacted with the catalyst in (iii) further contains an inert gas in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, and more preferably from 37 to 43 vol.-%. It is particularly preferred according to the present invention that the gas stream provided in (ii) and contacted with the catalyst in (iii) contains from 39 to 41 vol.-% of inert gas.

The type of inert gas which may be employed in the inventive process is not particularly restricted provided that under the chosen conditions it allows the conversion of 2-aminoethanol to ethane-1,2-diamine and/or linear polyethylenimines. Thus, by way of example, the inert gas may comprise one or more gases selected from the group consisting of noble gases, $N_2$, and mixtures of two or more thereof, preferably from the group consisting of He, Ne, Ar, $N_2$, and mixtures of two or more thereof, more preferably Ar and/or $N_2$, preferably $N_2$. It is, however, particularly preferred according to the present invention that the inert gas is Ar and/or $N_2$, preferably $N_2$.

According to the present invention, there is in principle no restriction as to the content of water in the gas stream provided in (ii) and contacted with the catalyst in (iii), provided that the content of $H_2O$ is of 5 vol.-% or less. Thus, by way of example, the amount of $H_2O$ in the gas stream provided in (ii) and contacted with the catalyst in (iii) may be of 3 vol.-% or less, preferably of 1 vol.-% or less, more preferably of 0.5 vol.-% or less, more preferably of 0.1 vol.-% or less, more preferably of 0.05 vol.-% or less, more preferably of 0.01 vol.-% or less, more preferably of 0.005 vol.-% or less, more preferably of 0.001 vol.-% or less, more preferably of 0.0005 vol.-% or less. It is, however, particularly preferred according to the present invention that the gas stream provided in (ii) and contacted with the catalyst in (iii) contains 0.0001 vol.-% or less of water, preferably no water.

According to the present invention, the gas stream provided in (ii) is preferably heated prior to contacting with the catalyst in (iii). Thus, by way of example, the gas stream provided in (ii) may be heated at a temperature in the range of from 120 to 600° C., prior to contacting with the catalyst in (iii) at that temperature, preferably in the range of from 150 to 550° C., more preferably from 200 to 500° C., more preferably from 230 to 450° C., more preferably from 250 to 400° C., more preferably from 270 to 370° C., more preferably from 300 to 350° C., more preferably from 320 to 340° C. It is, however, particularly preferred according to the present invention that the gas stream provided in (ii) is heated at a temperature of from 325 to 335° C. prior to contacting with the catalyst in (iii) at that temperature.

According to the present invention, there is in principle no restriction as to the conditions for contacting the catalyst with the gas stream in (iii) provided that the conversion 2-aminoethanol to ethane-1,2-diamine and/or linear polyethylenimines takes place. Thus, by way of example, the contacting of the catalyst with the gas stream in (iii) may be effected at a pressure in the range of from 0.05 to 20 MPa, preferably from 0.1 to 10 MPa, more preferably from 0.3 to 5 MPa, more preferably from 0.5 to 3 MPa, more preferably from 0.6 to 2 MPa, more preferably from 0.7 to 1.5 MPa, more preferably from 0.8 to 1.3 MPa. It is, however, particularly preferred according to the present invention that the contacting of the catalyst with the gas stream in (iii) is effected in the range of from 0.9 to 1.1 MPa.

As regards the gas hourly space velocity (GHSV) used for contacting of the catalyst with the gas stream in (iii), no particular restrictions apply such that in principle any conceivable gas hourly space velocity may be chosen for conducting the inventive process, provided that it is comprised in the range of from 100 to 30,000 $h^{-1}$. Thus, by way of example, the contacting of the catalyst with the gas stream in (iii) may be effected at a gas hourly space velocity (GHSV) in the range of from 500 to 20,000 $h^{-1}$, preferably from 1,000 to 15,000 $h^{-1}$, more preferably from 2,000 to 10,000 $h^{-1}$, more preferably from 3,000 to 8,000 $h^{-1}$, more preferably from 4,000 to 6,000 $h^{-1}$, more preferably from 4,500 to 5,500 $h^{-1}$. It is, however, particularly preferred according to the present invention that the contacting of the catalyst with the gas stream in (iii) is effected at a gas hourly space velocity (GHSV) in the range of from 4,800 to 5,200 $h^{-1}$.

According to the present invention, there is in principle no restriction as to the $YO_2:X_2O_3$ molar ratio of the zeolitic material such that in principle any conceivable $YO_2:X_2O_3$ molar ratio may be chosen for conducting the inventive process. Thus, by way of example, the zeolitic material may display a $YO_2:X_2O_3$ molar ratio of from 5 to 100, preferably from 6 to 70, more preferably from 8 to 40, more preferably from 10 to 30, more preferably from 12 to 25, more preferably from 14 to 20. It is, however, particularly preferred according to the present invention that the zeolitic material displays a $YO_2:X_2O_3$ molar ratio of from 15 to 17.

As regards the tetravalent element Y of the zeolitic material used in the inventive process, no particular restrictions apply such that in principle any conceivable tetravalent element may be chosen for conducting the inventive process. Thus, by way of example, Y may be selected from the group consisting of Si, Sn, Ti, Zr, Ge, and mixtures of two or more thereof. It is, however, particularly preferred according to the present invention that Y is Si.

As regards the trivalent element X of the zeolitic material used in the inventive process, no particular restrictions apply such that in principle any conceivable trivalent element may be chosen for conducting the inventive process. Thus, by way of example, X may be selected from the group consisting of Al, B, In, Ga, and mixtures of two or more thereof. It is, however, preferred according to the present invention that X is Al and/or B, and preferably Al.

According to the present invention, there is in principle no restriction as to the content of copper as extra-framework in the zeolitic material. Thus, by way of example, the zeolitic material may contain from 0.5 to 15 wt.-% of copper as extra-framework ions calculated as the element and based on 100 wt-% of $YO_2$ contained in the zeolitic material having the MOR framework structure, preferably from 1 to 10 wt.-%, more preferably from 1.3. to 8 wt.-%, more preferably from 1.5 to 7 wt.-%, more preferably from 1.8 to 6 wt.-%, more preferably from 2 to 5.5 wt.-%, more preferably from 2.3 to 5 wt.-%, more preferably from 2.5 to 4.5 wt.-%, more preferably from 2.8 to 4 wt.-%, more preferably from 3 to 3.5 wt.-%. It is, however, particularly preferred according to the present invention that the zeolitic material contains from 3.1 to 3.4 wt.-% of copper as extra-framework ions calculated as the element and based on 100 wt-% of $YO_2$ contained in the zeolitic material having the MOR framework structure.

According to the present invention, it is preferred that the $Cu:X_2O_3$ molar ratio of the zeolitic material is in the range of from 0.01 to 2, preferably from 0.05 to 1.5, more preferably from 0.1 to 1, more preferably from 0.2 to 0.8, more preferably from 0.3 to 0.7, more preferably from 0.35 to 0.65, more preferably from 0.4 to 0.6. It is particularly preferred that the $Cu:X_2O_3$ molar ratio of the zeolitic material is in the range of from 0.45 to 0.55.

It is preferred according to the present invention that the zeolitic material having the MOR framework structure comprises one or more zeolites selected from the group consisting of Mordenite, UZM-14, [Ga—Si—O]-MOR, Ca-Q, LZ-211, Maricopaite, Na-D, RMA-1, and mixtures of two or more thereof, wherein preferably the zeolitic material having the MOR framework structure is UZM-14 and/or Mordenite. It is particularly preferred according to the present invention that the zeolitic material having the MOR framework structure is Mordenite.

According to the present invention, it is preferred that the zeolitic material contains substantially no Na, preferably substantially no Na or K, more preferably substantially no alkali metal. It is particularly preferred according to the present invention that the zeolitic material contains substantially no alkali metal or alkaline earth metals.

Within the meaning of the present invention, "substantially" as employed in the present invention with respect to the amount of Na, K, alkali metals or alkaline earth metals contained in the framework of the zeolitic material indicates an amount of 0.1 wt.-% or less of Na, K, alkali metals or alkaline earth metals calculated as the element and based on 100 wt.-% of $YO_2$ contained in the zeolitic material having the MOR framework structure, preferably 0.05 wt.-% or less, more preferably 0.001 wt.-% or less, more preferably 0.0005 wt.-% or less, and even more preferably 0.0001 wt.-% or less thereof.

According to the present invention, it is preferred that the gas stream obtained in (iii) after contacting of the gas stream provided in (ii) with the catalyst provided in (i) displays an (ethane-1,2-diamine+diethylenetriamine):(aminoethylethanolamine+piperazine) molar ratio of the total molar amount of ethane-1,2-diamine and diethylenetriamine to the total molar amount of aminoethylethanolamine and piperazine of more than 5, preferably of 5 to 80, more preferably of 5.5 to 50, more preferably of 6 to 30, more preferably of 6.5 to 20, more preferably of 7 to 15, more preferably of 7.5 to 12, more preferably of 8 to 11, more preferably of 8.5 to 10.5. It is particularly preferred according to the present invention that the gas stream obtained in (iii) after contacting of the gas stream provided in (ii) with the catalyst provided in (i)

displays an (ethane-1,2-diamine+diethylenetriamine):(aminoethylethanolamine+piperazine) molar ratio of the total molar amount of ethane-1,2-diamine and diethylenetriamine to the total molar amount of aminoethylethanolamine and piperazine of 9 to 10.

According to the present invention, it is preferred that at no point prior to the contacting in (iii) of the catalyst provided in (i) with the gas stream provided in (ii) has the zeolitic material having the MOR framework structure been subject to a treatment for the removal of $X_2O_3$ from its framework structure, and preferably to a treatment for the removal of $X_2O_3$ from the zeolitic material.

Within the meaning of the present invention, wherein preferably at no point prior to the contacting in (iii) of the catalyst provided in (i) with the gas stream provided in (ii) has the zeolitic material having the MOR framework structure been subject to a treatment for the removal of $X_2O_3$ from its framework structure, this indicates that at no point has the zeolitic material been subject to a treatment wherein 5 mole-% or more of $X_2O_3$ based on 100 mole-% of $X_2O_3$ contained in the zeolitic material as synthesized has been removed from the framework structure of the zeolitic material, preferably 3 mole-% or more, more preferably 1 mole-% or more, more preferably 0.5 mole-% or more, more preferably 0.1 mole-% or more, more preferably 0.05 mole-% or more, more preferably 0.01 mole-% or more, more preferably 0.005 mole-% or more, more preferably 0.001 mole-% or more, more preferably 0.0005 mole-% or more, and more preferably 0.0001 mole-% or more.

According to the meaning of the present invention wherein it is preferred that at no point prior to the contacting in (iii) of the catalyst provided in (i) with the gas stream provided in (ii) has the zeolitic material having the MOR framework structure been subject to a treatment for the removal of $X_2O_3$ from the zeolitic material, this indicates that at no point has the zeolitic material been subject to a treatment wherein 5 mole-% or more of $X_2O_3$ based on 100 mole-% of $X_2O_3$ contained in the zeolitic material as synthesized has been removed from the zeolitic material, preferably 3 mole-% or more, more preferably 1 mole-% or more, more preferably 0.5 mole-% or more, more preferably 0.1 mole-% or more, more preferably 0.05 mole-% or more, more preferably 0.01 mole-% or more, more preferably 0.005 mole-% or more, more preferably 0.001 mole-% or more, more preferably 0.0005 mole-% or more, and more preferably 0.0001 mole-% or more.

As regards the preparation of the zeolitic material having the MOR framework structure used in the inventive process, no particular restrictions apply such that in principle any conceivable zeolitic material having the MOR framework structure may be chosen for conducting the inventive process. It is, however, preferred according to the present invention that the zeolitic material having the MOR framework structure is prepared by a process comprising (1) preparing a mixture comprising at least one source of $YO_2$, at least one source of $X_2O_3$, and comprising one or more organotemplates as structure directing agent and/or comprising seed crystals;

(2) crystallizing the mixture prepared in (i) for obtaining a zeolitic material having the MOR framework structure;

(3) optionally isolating the zeolitic material obtained in (2);

(4) optionally washing the zeolitic material obtained in (2) or (3);

(5) optionally drying and/or calcining the zeolitic material obtained in (2), (3), or (4);

(6) optionally subjecting the zeolitic material obtained in (2), (3), (4), or (5) to an ion-exchange procedure, wherein extra-framework ions contained in the zeolitic material are ion-exchanged against $H^+$;

(7) subjecting the zeolitic material obtained in (2), (3), (4), (5), or (6) to an ion-exchange procedure, wherein extra-framework ions contained in the zeolitic material are ion-exchanged against $Cu^{2+}$ and/or $Cu^+$, preferably against $Cu^{2+}$;

(8) optionally drying and/or calcining the zeolitic material obtained in (7).

Within the meaning of the present invention, the term "organotemplate" as employed in the present application generally designates any conceivable organic material which is suitable for template-mediated synthesis of a zeolite material, preferably of a zeolite material having a MOR-type framework-structure, and even more preferably which is suitable for the synthesis of Mordenite. It is preferred according to the present invention that the one or more organotemplates comprised in the mixture prepared in (1) is selected from the group consisting of tetraalkylammonium containing compounds and tetraalkylphosphonium containing compounds, preferably from the group consisting of tetraalkylammonium cation $R^1R^2R^3R^4N^+$-containing compounds and tetraalkylphosphonium cation $R^1R^2R^3R^4P^+$-containing compounds, wherein $R^1$, $R^2$, $R^3$, and $R^4$ independently from one another stand for optionally substituted and/or optionally branched $(C_1-C_6)$alkyl, preferably $(C_1-C_5)$alkyl, more preferably $(C_1-C_4)$alkyl, more preferably $(C_1-C_3)$alkyl, and even more preferably for optionally substituted methyl or ethyl, wherein even more preferably $R^1$, $R^2$, $R^3$, and $R^4$ stand for optionally substituted ethyl, preferably for unsubstituted ethyl.

It is further preferred according to the present invention that the one or more tetraalkylammonium cation $R^1R^2R^3R^4N^+$-containing compounds and/or that the one or more tetraalkylphosphonium cation $R^1R^2R^3R^4P^+$-containing compounds are salts, preferably one or more salts selected from the group consisting of halides, preferably chloride and/or bromide, more preferably chloride, hydroxide, sulfate, nitrate, phosphate, acetate, and mixtures of two or more thereof, more preferably from the group consisting of chloride, hydroxide, sulfate, and mixtures of two or more thereof, more preferably the one or more tetraalkylammonium cation $R^1R^2R^3R^4N^+$-containing compounds and/or the one or more tetraalkylphosphonium cation $R^1R^2R^3R^4P^+$-containing compounds are hydroxides and/or bromides, and even more preferably bromides.

According to the present invention, it is preferred that the one or more organotemplates comprised in the mixture prepared in (1) is selected from the group consisting of N,N,N,N-tetra($C_1-C_4$)alkylammonium and N,N,N,N-tetra($C_1-C_4$)alkylphosphonium compounds, preferably from the group consisting of N,N,N,N-tetra($C_1-C_3$)alkylammonium and N,N,N,N-tetra($C_1-C_3$)alkylphosphonium compounds, more preferably from the group consisting of N,N,N,N-tetra($C_1-C_2$)alkylammonium and N,N,N,N-tetra($C_1-C_2$)alkylphosphonium compounds, more preferably from the group consisting of N,N,N,N-tetra($C_1-C_2$)alkylammonium and N,N,N,N-tetra($C_1-C_2$)alkylphosphonium compounds, more preferably from the group consisting of N,N,N,N-tetraethylammonium compounds, N,N,N,N-tetramethylammonium compounds, N,N,N,N-tetraethylphosphonium compounds, N,N,N,N-tetramethylphosphonium compounds, and mixtures of two or more thereof. It is particularly preferred according to the present invention that the one or more organotemplates comprise one or more N,N, N,N-tetraethylammonium or N,N,N,N-tetraethylphosphonium compounds, preferably one or more N,N,N,N-tetraethylammonium compounds.

As regards the organotemplate:$YO_2$ molar ratio of the one or more organotemplates to $YO_2$ in the mixture provided according to (1) for preparing the zeolitic material having the MOR framework structure, no particular restrictions apply such that in principle any conceivable organotemplate:$YO_2$ molar ratio may be chosen for conducting the process for preparing the zeolitic material having the MOR framework structure. Thus, by way of example, the organotemplate:$YO_2$ molar ratio of the one or more organotemplates to $YO_2$ in the mixture provided according to (1) may range from 0.005 to 0.14, preferably from 0.01 to 0.3, more preferably from 0.02 to 0.2, more preferably from 0.025 to 0.14, more preferably from 0.03 to 0.1, more preferably from 0.035 to 0.08, more preferably from 0.04 to 0.06. It is, however, particularly preferred according to the present invention that the organotemplate:$YO_2$ molar ratio of the one or more organotemplates to $YO_2$ in the mixture provided according to (1) ranges from 0.045 to 0.055.

It is alternatively preferred that the mixture prepared in (1) and crystallized in (2) contains substantially no organotemplate with the exception of organotemplate which may optionally be contained in the micropores of the zeolitic material preferably employed as seed crystals, wherein more preferably the mixture prepared in (1) and crystallized in (2) contains substantially no organotemplate. It is, however, preferred according to the present invention that the mixture prepared in (1) comprises one or more organotemplates as structure directing agent.

Within the meaning of the present invention, wherein the mixture prepared in (1) and crystallized in (2) contains substantially no organotemplates, this indicates that the mixture prepared in (1) and crystallized in (2) may only contain organotemplates in an amount of 0.1 wt.-% or less based on 100 wt.-% of $YO_2$ contained in the mixture, and preferably in an amount of 0.05 wt.-% or less, more preferably of 0.001 wt.-% or less, more preferably of 0.0005 wt.-% or less, and even more preferably in an amount of 0.0001 wt.-% or less based on 100 wt.-% of $YO_2$ contained in the mixture. Said amounts of organotemplates, if at all present in the mixture prepared in (1) and crystallized in (2), may also be denoted as "impurities" or "trace amounts" within the meaning of the present invention. Furthermore, it is noted that the terms "organotemplate" and "organic structure directing agent" are synonymously used in the present application.

It is preferred according to the present invention that the mixture prepared in (1) and crystallized in (2) of the process for preparing the zeolitic material having the MOR framework structure used in the inventive process contains substantially no zeolitic material. It is particularly preferred according to the present invention that the mixture prepared in (1) and crystallized in (2) contains substantially no seed crystals.

Within the meaning of the present invention, wherein the mixture prepared in (1) and crystallized in (2) contains substantially no zeolitic material and preferably contains substantially no seed crystals, this indicates that the mixture prepared in (1) and crystallized in (2) may only contain zeolitic material and preferably may only contain seed crystals in an amount of 0.1 wt.-% or less based on 100 wt.-% of $YO_2$ contained in the mixture, and preferably in an amount of 0.05 wt.-% or less, more preferably of 0.001 wt.-% or less, more preferably of 0.0005 wt.-% or less, and even more preferably in an amount of 0.0001 wt.-% or less based on 100 wt.-% of $YO_2$ contained in the mixture. Said amounts of zeolitic material and preferably of seed crystals, if at all present in the mixture prepared in (1) and crystallized in (2), may also be denoted as "impurities" or "trace amounts" within the meaning of the present invention.

According to the present invention, it is preferred that in (6) of the process for preparing the zeolitic material having the MOR framework structure used in the inventive process the step of subjecting the zeolitic material to an ion-exchange procedure includes the steps of (6.a) subjecting the zeolitic material obtained in (2), (3), (4), or (5) to an ion-exchange procedure, wherein extra-framework ions contained in the zeolitic material are ion-exchanged against $NH_4^+$;

(6.b) calcining the ion-exchanged zeolitic material obtained in (6.a) for obtaining the H-form of the zeolitic material.

As regards calcining in (5), (6.b), (8) and/or (12), no particular restrictions apply such that in principle any conceivable temperature and/or duration may be chosen for conducting the process for preparing the zeolitic material having the MOR framework structure.

Thus, by way of example, calcining in (5), (6.b), (8) and/or (12) may be conducted at a temperature in the range of from 200 to 850° C., preferably of from 250 to 800° C., more preferably of from 300 to 750° C., more preferably of from 350 to 700° C., more preferably of from 400 to 650° C., more preferably of from 450 to 620° C., more preferably of from 500 to 600° C., and more preferably of from 520 to 580° C. It is, however, particularly preferred according to the present invention that calcining in (5), (6.b), (8) and/or (12) is conducted at a temperature in the range of from 540 to 560° C.

Further, by way of example, calcining of the zeolitic material in (5), (6.b), (8) and/or (12) may be effected in batch mode, in semi-continuous mode, or in continuous mode. Calcination in (6.b) is performed by heating of the zeolitic material to a temperature according to any of the particular and performed embodiments defined in the present application and holding it at that temperature for a duration ranging from 0.5 to 36 h, preferably from 1 to 32 h, more preferably from 2 to 28 h, more preferably from 4 to 24 h, more preferably from 6 to 20 h, more preferably from 8 to 18 h, and more preferably from 10 to 14 h. It is, however, particularly preferred according to the present invention that calcining in (5), (6.b), (8) and/or (12) is effected by heating the zeolitic material to a given temperature and holding it at that temperature for a duration ranging from 11.5 to 12.5 h. Furthermore, it is particularly preferred that calcining in (5), (6.b), (8) and/or (12) is conducted at a temperature in the range of from 540 to 560° C. for a duration ranging from 11.5 to 12.5 h. When conducted in semi-continuous or in continuous mode, the duration of calcination corresponds to the residence time of the zeolitic material in the given calciner operating in a semi-continuous mode or in continuous mode.

In case the process is carried out in a larger scale, it is preferred to perform the calcination in semi-continuous mode or in continuous mode, more preferably in continous mode. Even more preferably, calcining the zeolitic material in (5), (6.b), (8) and/or (12) is carried out in continuous mode with a rate in the range of from 0.2 to 50.0 kg of the zeolitic material per hour, preferably from 0.5 to 2.0 kg of the zeolitic material per hour. Conceivable apparatuses which can be used for such a preferred continuous calcination include, for example, a band calciner and/or a rotary calciner, wherein preferably a rotary calciner is used.

According to the present invention, it is however particularly preferred that, if the copper ion-exchanged zeolitic material obtained in (7) is subject to a heating treatment such as drying and/or calcination, said treatment does not involve a temperature of 540° C. or greater, and preferably does not involve a temperature of 520° C. or greater, more preferably of 500° C. or greater, more preferably of 450° C. or greater, more preferably of 400° C. or greater, more preferably of 350° C. or greater, more preferably of 300° C. or greater, more preferably of 250° C. or greater, and more preferably of 200° C. According to the present invention it is particularly preferred that the copper ion-exchanged zeolitic material obtained in (7) is not subject to a temperature of 150° C. or greater. Thus, according to said particularly preferred embodiments, the copper ion-exchanged zeolitic material obtained in (7) is not subject to calcination according to (8) as defined in any of the particular and preferred embodiments of the present application.

It is preferred according to the present invention that in (7) the zeolitic material is ion-exchanged such as to obtain a loading of Cu in the zeolitic material ranging from 0.1 to 10 wt.-% calculated as the element and based on 100 wt.-% of $YO_2$ contained in the zeolitic material, preferably from 0.5 to 8 wt.-%, more preferably from 1 to 6 wt.-%, more preferably from 1.2 to 5 wt.-%, more preferably from 1.5 to 4 wt.-%, more preferably from 1.8 to 3.5 wt.-%, more preferably from 2 to 3 wt.-%, more preferably from 2.3 to 2.9 wt.-%. It is particularly preferred according to the present invention that in (7) the zeolitic material is ion-exchanged such as to obtain a loading of Cu in the zeolitic material ranging from 2.5 to 2.7 wt.-%.

As regards the element Y used for preparing the zeolitic material having the MOR framework structure, no particular restrictions apply such that in principle any conceivable tetravalent element may be chosen for conducting the process for preparing the zeolitic material having the MOR framework structure. Thus, by way of example, Y may be selected from the group consisting of Si, Sn, Ti, Zr, Ge, and combinations of two or more thereof. It is, however, particularly preferred that Y is Si.

It is preferred according to the present invention that at least one source for $YO_2$ comprises one or more compounds selected from the group consisting of silicas, silicates, and mixtures thereof, preferably from the group consisting of fumed silica, silica hydrosols, reactive amorphous solid silicas, silica gel, silicic acid, water glass, sodium metasilicate hydrate, sesquisilicate, disilicate, colloidal silica, silicic acid esters, tetraalkoxysilanes, and mixtures of two or more thereof, more preferably from the group consisting of fumed silica, silica hydrosols, silica gel, silicic acid, water glass, colloidal silica, silicic acid esters, tetraalkoxysilanes, and mixtures of two or more thereof, more preferably from the group consisting of fumed silica, silica hydrosols, silica gel, colloidal silica, and mixtures of two or more thereof, more preferably from the group consisting of fumed silica, silica gel, colloidal silica, and mixtures of two or more thereof, more preferably the at least one source of $YO_2$ is selected from the group consisting of fumed silica, colloidal silica, and mixtures thereof. It is particularly preferred according to the present invention that fumed silica is employed as the source of $YO_2$.

As regards the element X used for preparing the zeolitic material having the MOR framework structure, no particular restrictions apply such that in principle any conceivable trivalent element may be chosen for conducting the process for preparing the zeolitic material having the MOR framework structure. Thus, by way of example, X may be selected from the group consisting of Al, B, In, Ga, and combinations of two or more thereof. It is, however, preferred according to the present invention that X is Al.

According to the present invention, it is preferred that the at least one source for $X_2O_3$ comprises one or more aluminum salts, preferably an aluminate of an alkali metal, wherein the alkali metal is preferably selected from the group consisting of Li, Na, K, Rb, and Cs, wherein more preferably the alkali metal is Na and/or K, and wherein even more preferably the alkali metal is Na.

As regards the $YO_2:X_2O_3$ molar ratio of the mixture prepared in (1), no particular restrictions apply such that in principle any conceivable $YO_2:X_2O_3$ molar ratio may be chosen for conducting the process for preparing the zeolitic material having the MOR framework structure used in the inventive process. Thus, by way of example, the $YO_2:X_2O_3$ molar ratio of the mixture prepared in (1) may range from 2 to 50, preferably from 4 to 40, more preferably from 6 to 35, more preferably from 10 to 30, more preferably from 13 to 25, more preferably from 15 to 23, more preferably from 17 to 22. It is, however, particularly preferred according to the present invention that the $YO_2:X_2O_3$ molar ratio of the mixture prepared in (1) ranges from 19 to 21.

As regards the seed crystals used for the process of preparing the zeolitic material having the MOR framework structure, no particular restrictions apply such that in principle any conceivable seed crystals may be chosen for preparing the zeolitic material having the MOR framework structure. Thus, by way of example, the seed crystals may comprise a zeolitic material, preferably one or more zeolites, more preferably one or more zeolites having a BEA framework structure, more preferably the seed crystals comprise zeolite beta. It is, however, particularly preferred according to the present invention that zeolite beta is employed as the seed crystals for preparing the mixture in (1).

Same applies to the amount of seed crystals used for the process of preparing the zeolitic material having the MOR framework structure provided that the zeolitic material having the MOR framework structure can be prepared. Thus, by way of example, the amount of seed crystals in the mixture prepared in (1) may range from 0.1 to 15 wt.-% based on 100 wt.-% of $YO_2$ contained in the mixture, preferably from 0.5 to 10 wt.-%, more preferably from 0.8 to 8 wt.-%, more preferably from 1 to 5 wt.-%, and more preferably from 1.3 to 3 wt.-%. It is, however, particularly preferred according to the present invention that the amount of seed crystals in the mixture prepared in (1) ranges from 1.5 to 2.5 wt.-%.

It is preferred according to the present invention that the mixture prepared in (1) further comprises a solvent system containing one or more solvents, wherein the solvent system preferably comprises one or more solvents selected from the group consisting of polar protic solvents and mixtures thereof, preferably from the group consisting of n-butanol, isopropanol, propanol, ethanol, methanol, water, and mixtures thereof, more preferably from the group consisting of ethanol, methanol, water, and mixtures thereof, wherein more preferably the solvent system comprises water. It is particularly preferred according to the present invention that water, preferably deionized water, is used as the solvent system.

According to the present invention, it is further preferred that when the mixture prepared in (1) and crystallized in (2) comprises one or more organotemplates and when the mixture prepared in (1) comprises water as the solvent system, the $H_2O:YO_2$ molar ratio of the mixture prepared in (1) may range from 5 to 70, preferably from 10 to 65, more preferably from 15 to 60, more preferably from 20 to 55, more preferably from 25 to 50, more preferably from 30 to 47, more preferably from 35 to 45, and more preferably from 37 to 43. It is, however, particularly preferred according to the present invention that when the mixture prepared in (1) and crystallized in (2) comprises one or more organotemplates and when the mixture prepared in (1) comprises water as the solvent system, the $H_2O:YO_2$ molar ratio of the mixture prepared in (1) ranges from 39 to 41.

It is further preferred according to the present invention that when the mixture prepared in (1) and crystallized in (2) comprises seed crystals and when the mixture prepared in (1) comprises water as the solvent system, the $H_2O:YO_2$ molar ratio of the mixture prepared in (1) may range from 5 to 45, preferably from 10 to 40, more preferably from 12 to 35, more preferably from 15 to 30, more preferably from 17 to 27, and more preferably from 19 to 25. It is, however, particularly preferred according to the present invention that when the mixture prepared in (1) and crystallized in (2) comprises seed crystals and when the mixture prepared in (1) comprises water as the solvent system, the $H_2O:YO_2$ molar ratio of the mixture prepared in (1) ranges from 21 to 23.

It is preferred according to the present invention that the mixture prepared in (1) further comprises one or more alkali metals (AM), preferably the one or more alkali metals are selected from the group consisting of Li, Na, K, Cs, and mixtures thereof, more preferably the mixture prepared in (1) further comprises Na and/or K. It is particularly preferred according to the present invention that the mixture prepared in (1) further comprises Na as the alkali metal AM.

It is further preferred according to the present invention that when the mixture prepared in (1) and crystallized in (2) comprises one or more organotemplates, the $AM:YO_2$ molar ratio of alkali metals to $YO_2$ in the mixture prepared in (1) ranges from 0.05 to 2, preferably from 0.1 to 1.5, more preferably from 0.2 to 1, more preferably from 0.3 to 0.7, more preferably from 0.35 to 0.65, more preferably from 0.4 to 0.6. It is particularly preferred according to the present invention that when the mixture prepared in (1) and crystallized in (2) comprises one or more organotemplates, the $AM:YO_2$ molar ratio of alkali metals to $YO_2$ in the mixture prepared in (1) ranges from 0.45 to 0.55.

It is further preferred according to the present invention that when the mixture prepared in (1) and crystallized in (2) comprises seed crystals, the $AM:YO_2$ molar ratio of alkali metals to $YO_2$ in the mixture prepared in (1) ranges from 0.3 to 2, preferably from 0.5 to 1.5, more preferably from 0.8 to 1.2, more preferably from 1 to 1, more preferably from 1.2 to 0.8, more preferably from 1.3 to 0.5. It is particularly preferred according to the present invention that when the mixture prepared in (1) and crystallized in (2) comprises seed crystals, the $AM:YO_2$ molar ratio of alkali metals to $YO_2$ in the mixture prepared in (1) ranges from 1.35 to 1.4.

According to the present invention, it is further preferred that the $YO_2:X_2O_3:AM$ molar ratio of the mixture prepared in (1) ranges from 1:(0.02-0.5):(0.05-2), preferably from 1:(0.025-0.25):(0.05-2), more preferably from 1:(0.029-0.17):(0.1-1.5), more preferably from 1:(0.033-0.1):(0.2-1), more preferably from 1:(0.04-0.08):(0.3-0.7), more preferably from 1:(0.043-0.7):(0.35-0.65), more preferably from 1:(0.045-0.06):(0.4-0.6), and more preferably from 1:(0.045-0.05):(0.45-0.55).

As regards the crystallization in (2), no particular restrictions apply such that in principle any conceivable conditions for crystallization may be chosen for conducting the process of preparing the zeolitic material having the MOR framework structure.

Thus, by way of example, the crystallization in (2) may involve heating of the mixture prepared in (1), preferably to a temperature ranging from 75 to 210° C., more preferably from 100 to 200° C., more preferably from 130 to 190° C., more preferably from 150 to 185° C., more preferably from 160 to 180° C. It is, however, particularly preferred according to the present invention that the crystallization in (2) involves heating of the mixture prepared in (1) to a temperature ranging from 165 to 175° C.

By way of example, the crystallization in (2) may be conducted under autogenous pressure, preferably under solvothermal conditions. It is, however, particularly preferred according to the present invention that the crystallization in (2) is conducted under hydrothermal conditions.

Further, by way of example, the crystallization in (2) may involve heating of the mixture prepared in (1) for a period in the range of from 60 to 120 h, more preferably from 65 to 100 h, more preferably from 70 to 95 h, more preferably from 75 to 90 h, more preferably from 80 to 88 h. It is, however, particularly preferred according to the present invention that the crystallization in (2) involves heating of the mixture prepared in (1) for a period in the range of from 82 to 86 h.

According to the present invention, it is preferred that the zeolitic material having an MOR framework structure crystallized in (2) is Mordenite.

It is preferred according to the present invention that the mixture prepared in (1) and crystallized in (2) contains substantially no phosphorous.

Within the meaning of the present invention, "substantially" as employed in the present invention with respect to the amount of phosphorous contained in the mixture prepared in (1) and crystallized in (2) indicates an amount of 0.1 wt.-% or less of phosphorous calculated as the element and based on 100 wt.-% of $YO_2$ in the mixture, preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the mixture prepared in (1) and crystallized in (2) comprises both elemental phosphorous as well as phosphorous containing compounds.

Furthermore, it is preferred according to the present invention that the framework of the zeolitic material obtained in (2) contains substantially no phosphorous. It is particularly preferred that the zeolitic material obtained in (2) contains substantially no phosphorous.

Within the meaning of the present invention, "substantially" as employed in the present invention with respect to the amount of phosphorous contained in the framework of the zeolitic material obtained in (2) indicates an amount of 0.1 wt.-% or less of phosphorous calculated as the element and based on 100 wt.-% of $YO_2$ in the zeolitic material, preferably 0.05 wt.-% or less, more preferably 0.001 wt.-% or less, more preferably 0.0005 wt.-% or less, and even more preferably 0.0001 wt.-% or less thereof. Furthermore, within the meaning of the present invention, "substantially" as employed in the present invention with respect to the amount of phosphorous contained in the zeolitic material obtained in (2) indicates an amount of 0.1 wt.-% or less of phosphorous calculated as the element and based on 100 wt.-% of $YO_2$ in the zeolitic material, and preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the framework of the zeolitic material obtained in (2) and preferably not being contained in the mixture prepared in (1) and crystallized in (2) comprises both elemental phosphorous as well as phosphorous containing compounds.

There is no particular restriction according to the present invention as to the form in which the zeolitic material having the MOR framework structure and containing copper as extra-framework ions may be provided in the catalyst employed in the inventive process. Thus, the zeolitic material may be used as such, or may be employed together with further components. According to the inventive process it is thus preferred that the zeolitic material is comprised in the catalyst employed in the inventive process in the form of a molding. Accordingly it is preferred according to the present invention that the preferred process for preparing the zeolitic material according to any of the particular preferred embodiments described in the present application further comprises (9) mixing the copper ion-exchanged zeolitic material obtained in (7) or (8) with one or more binders;

(10) kneading of the mixture obtained in (9);

(11) molding of the kneaded mixture obtained in (10) to obtain one or more moldings; and

(12) drying and/or calcining the one or more moldings obtained in (11).

With respect to the one or more binders with which the copper ion-exchanged zeolitic material obtained in (7) or (8) may be mixed, no particular restrictions apply such that in principle any suitable binder may be employed. Thus, by way of example, the one or more binders may be selected from the group consisting of inorganic binders, wherein according to the present invention it is preferred that the one or more binders comprise one or more sources of a metal oxide and/or of a metalloid oxide or one or more sources of graphite, wherein the one or more sources of a metal oxide and/or of a metalloid oxide are preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, and mixtures of two or more thereof. According to the present invention it is however particularly preferred that the one or more binders comprise one or more sources of silica, alumina, zirconia, and/or graphite, wherein more preferably the binder consists of one or more sources of silica, alumina, zirconia, and/or graphite, wherein more preferably the one or more binders comprise one or more sources of silica, alumina, and/or zirconia, wherein even more preferably the binder consists of one or more sources silica, alumina, and/or zirconia, preferably of silica, alumina, and/or zirconia.

According to the present invention, it is preferred that 2-aminoethanol comprised in the gas stream obtained in (iii) is separated from said gas stream and recycled to (ii).

The present invention is further characterized by the following and particular preferred embodiments, including the combination and embodiments indicated by the respective dependencies:

1. A process for the conversion of 2-aminoethanol to ethane-1,2-diamine and/or linear polyethylenimines of the formula $H_2N-[CH_2CH_2NH]_n-CH_2CH_2NH_2$ wherein n≥1 comprising
   (i) providing a catalyst comprising a zeolitic material having the MOR framework structure comprising $YO_2$ and $X_2O_3$, wherein Y is a tetravalent element and X is a trivalent element, said zeolitic material containing copper as extra-framework ions;
   (ii) providing a gas stream comprising 2-aminoethanol and ammonia;
   (iii) contacting the catalyst provided in (i) with the gas stream provided in (ii) for converting 2-aminoethanol to ethane-1,2-diamine and/or linear polyethylenimines,
   wherein n preferably ranges from 1 to 8, more preferably from 1-5, more preferably from 1-4, more preferably from 1-3, more preferably from 1-2, wherein more preferably n=1.

2. The process of embodiment 1, wherein the gas stream provided in (ii) and contacted with the catalyst in (iii) contains 2-aminoethanol in an amount in the range of from 0.1 to 10 vol.-%, preferably from 0.5 to 5 vol.-%, more preferably from 1 to 4.5 vol.-%, more preferably from 1.5 to 4 vol.-%, more preferably from 2 to 3.7 vol.-%, more preferably from 2.5 to 3.5 vol.-%, more preferably from 2.7 to 3.3 vol.-%, and more preferably from 2.9 to 3.1 vol.-%.

3. The process of embodiment 1 or 2, wherein the ammonia:2-aminoethanol molar ratio in the gas stream provided in (ii) and contacted with the catalyst in (iii) is in the range of from 1 to 45, preferably from 2 to 35, more preferably from 4 to 30, more preferably from 6 to 25, more preferably from 8 to 20, more preferably from 10 to 16, and more preferably from 12 to 14.

4. The process of any of embodiments 1 to 3, wherein the gas stream provided in (ii) and contacted with the catalyst in (iii) contains ammonia in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%.

5. The process of any of embodiments 1 to 4, wherein the gas stream provided in (ii) and contacted with the catalyst in (iii) contains 1 vol.-% or less of hydrogen, preferably 0.5 vol.-% or less, more preferably 0.1 vol.-% or less, more preferably 0.05 vol.-% or less, more preferably 0.001 vol.-% or less, more preferably 0.0005 vol.-% or less, and more preferably 0.0001 vol.-% or less of hydrogen.

6. The process of any of embodiments 1 to 4, wherein the gas stream provided in (ii) and contacted with the catalyst in (iii) further contains hydrogen in an amount in the range of from 0.1 to 70 vol.-%, preferably from 0.5 to 50 vol.-%, more preferably from 1 to 40 vol.-%, more preferably from 5 to 35 vol.-%, more preferably from 10 to 30 vol.-%, more preferably from 15 to 25 vol.-%, more preferably from 17 to 23 vol.-%, and more preferably from 19 to 21 vol.-%.

7. The process of any of embodiments 1 to 6, wherein the gas stream provided in (ii) and contacted with the catalyst in (iii) further contains an inert gas in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%.

8. The process of embodiment 7, wherein the inert gas comprises one or more gases selected from the group consisting of noble gases, $N_2$, and mixtures of two or more thereof, preferably from the group consisting of He, Ne, Ar, $N_2$, and mixtures of two or more thereof, wherein more preferably the inert gas comprises Ar and/or $N_2$, preferably $N_2$, and wherein more preferably the inert gas is Ar and/or $N_2$, preferably $N_2$.

9. The process of any of embodiments 1 to 8, wherein the gas stream provided in (ii) and contacted with the catalyst in (iii) contains $H_2O$ in an amount of 5 vol.-% or less, preferably of 3 vol.-% or less, more preferably of 1 vol.-% or less, more preferably of 0.5 vol.-% or less, more preferably of 0.1 vol.-% or less, more preferably of 0.05 vol.-% or less, more preferably of 0.01 vol.-% or less, more preferably of 0.005 vol.-% or less, more preferably of 0.001 vol.-% or less, more preferably of 0.0005 vol.-% or less, and more preferably of 0.0001 vol.-% or less.

10. The process of any of embodiments 1 to 9, wherein the gas stream provided in (ii) is heated to a temperature in the range of from 120 to 600° C., prior to contacting with the catalyst in (iii) at that temperature, preferably in the range of from 150 to 550° C., more preferably from 200 to 500° C., more preferably from 230 to 450° C., more preferably from 250 to 400° C., more preferably from 270 to 370° C., more preferably from 300 to 350° C., more preferably from 320 to 340° C., and more preferably from 325 to 335° C.

11. The process of any of embodiments 1 to 10, wherein the contacting of the catalyst with the gas stream in (iii) is effected at a pressure in the range of from 0.05 to 20 MPa, preferably from 0.1 to 10 MPa, more preferably from 0.3 to 5 MPa, more preferably from 0.5 to 3 MPa, more preferably from 0.6 to 2 MPa, more preferably from 0.7 to 1.5 MPa, more preferably from 0.8 to 1.3 MPa, and more preferably from 0.9 to 1.1 MPa.

12. The process of any of embodiments 1 to 11, wherein the contacting of the catalyst with the gas stream in (iii) is effected at a gas hourly space velocity (GHSV) in the range of from 100 to 30,000 $h^{-1}$, preferably from 500 to 20,000 $h^{-1}$, more preferably from 1,000 to 15,000 $h^{-1}$, more preferably from 2,000 to 10,000 $h^{-1}$, more preferably from 3,000 to 8,000 $h^{-1}$, more preferably from 4,000 to 6,000 $h^{-1}$, more preferably from 4,500 to 5,500 $h^{-1}$, and more preferably from 4,800 to 5,200 $h^{-1}$.

13. The process of any of embodiments 1 to 12, wherein the zeolitic material displays a $YO_2:X_2O_3$ molar ratio in the range of from 5 to 100, preferably from 6 to 70, more preferably from 8 to 40, more preferably from 10 to 30, more preferably from 12 to 25, more preferably from 14 to 20, and more preferably from 15 to 17.

14. The process of any of embodiments 1 to 13, wherein Y is selected from the group consisting of Si, Sn, Ti, Zr, Ge, and mixtures of two or more thereof, Y preferably being Si.

15. The process of any of embodiments 1 to 14, wherein X is selected from the group consisting of Al, B, In, Ga, and mixtures of two or more thereof, X preferably being Al and/or B, and more preferably being Al.

16. The process of any of embodiments 1 to 15, wherein the zeolitic material contains from 0.5 to 15 wt.-% of copper as extra-framework ions calculated as the element and based on 100 wt-% of $YO_2$ contained in the zeolitic material having the MOR framework structure, preferably from 1 to 10 wt.-%, more preferably from 1.3. to 8 wt.-%, more preferably from 1.5 to 7 wt.-%, more preferably from 1.8 to 6 wt.-%, more preferably from 2 to 5.5 wt.-%, more preferably from 2.3 to 5 wt.-%, more preferably from 2.5 to 4.5 wt.-%, more preferably from 2.8 to 4 wt.-%, more preferably from 3 to 3.5 wt.-%, more preferably from 3.1 to 3.4 wt.-%.

17. The process of any of embodiments 1 to 16, wherein the $Cu:X_2O_3$ molar ratio of the zeolitic material is in the range of from 0.01 to 2, preferably from 0.05 to 1.5, more preferably from 0.1 to 1, more preferably from 0.2 to 0.8, more preferably from 0.3 to 0.7, more preferably from 0.35 to 0.65, more preferably from 0.4 to 0.6, more preferably from 0.45 to 0.55.

18. The process of any of embodiments 1 to 17, wherein the zeolitic material having the MOR framework structure comprises one or more zeolites selected from the group consisting of Mordenite, UZM-14, [Ga—Si—O]-MOR, Ca-Q, LZ-211, Maricopaite, Na-D, RMA-1, and mixtures of two or more thereof, wherein preferably the zeolitic material having the MOR framework structure is UZM-14 and/or Mordenite, preferably Mordenite.

19. The process of any of embodiments 1 to 18, wherein the zeolitic material contains substantially no Na, preferably substantially no Na or K, more preferably substantially no alkali metal, and more preferably substantially no alkali metal or alkaline earth metals.

20. The process of any of embodiments 1 to 19, wherein the gas stream obtained in (iii) after contacting of the gas stream provided in (ii) with the catalyst provided in (i) displays an (ethane-1,2-diamine+diethylenetriamine):(aminoethylethanolamine+piperazine) molar ratio of the total molar amount of ethane-1,2-diamine and diethylenetriamine to the total molar amount of aminoethylethanolamine and piperazine of more than 5, preferably of 5 to 80, more preferably of 5.5 to 50, more preferably of 6 to 30, more preferably of 6.5 to 20, more preferably of 7 to 15, more preferably of 7.5 to 12, more preferably of 8 to 11, more preferably of 8.5 to 10.5, and more preferably of 9 to 10.

21. The process of any of embodiments 1 to 20, wherein at no point prior to the contacting in (iii) of the catalyst provided in (i) with the gas stream provided in (ii) has the zeolitic material having the MOR framework structure been subject to a treatment for the removal of $X_2O_3$ from its framework structure, and preferably to a treatment for the removal of $X_2O_3$ from the zeolitic material.

22. The process of any of embodiments 1 to 21, wherein the zeolitic material having the MOR framework structure is prepared by a process comprising
   (1) preparing a mixture comprising at least one source of $YO_2$, at least one source of $X_2O_3$, and comprising one or more organotemplates as structure directing agent and/or comprising seed crystals;
   (2) crystallizing the mixture prepared in (i) for obtaining a zeolitic material having the MOR framework structure;
   (3) optionally isolating the zeolitic material obtained in (2);
   (4) optionally washing the zeolitic material obtained in (2) or (3);
   (5) optionally drying and/or calcining the zeolitic material obtained in (2), (3), or (4);

- (6) optionally subjecting the zeolitic material obtained in (2), (3), (4), or (5) to an ion-exchange procedure, wherein extra-framework ions contained in the zeolitic material are ion-exchanged against H$^+$;
- (7) subjecting the zeolitic material obtained in (2), (3), (4), (5), or (6) to an ion-exchange procedure, wherein extra-framework ions contained in the zeolitic material are ion-exchanged against Cu$^{2+}$ and/or Cu$^+$, preferably against Cu$^{2+}$;
- (8) optionally drying and/or calcining the zeolitic material obtained in (7).

23. The process of embodiment 22, wherein the one or more organotemplates comprised in the mixture prepared in (1) is selected from the group consisting of tetraalkylammonium containing compounds and tetraalkylphosphonium containing compounds, preferably from the group consisting of tetraalkylammonium cation $R^1R^2R^3R^4N^+$-containing compounds and tetraalkylphosphonium cation $R^1R^2R^3R^4P^+$-containing compounds, wherein $R^1$, $R^2$, $R^3$, and $R^4$ independently from one another stand for optionally substituted and/or optionally branched ($C_1$-$C_6$)alkyl, preferably ($C_1$-$C_5$) alkyl, more preferably ($C_1$-$C_4$)alkyl, more preferably ($C_1$-$C_3$)alkyl, and even more preferably for optionally substituted methyl or ethyl, wherein even more preferably $R^1$, $R^2$, $R^3$, and $R^4$ stand for optionally substituted ethyl, preferably for unsubstituted ethyl.

24. The process of embodiment 23, wherein the one or more tetraalkylammonium cation $R^1R^2R^3R^4N^+$-containing compounds and/or that the one or more tetraalkylphosphonium cation $R^1R^2R^3R^4P^+$-containing compounds are salts, preferably one or more salts selected from the group consisting of halides, preferably chloride and/or bromide, more preferably chloride, hydroxide, sulfate, nitrate, phosphate, acetate, and mixtures of two or more thereof, more preferably from the group consisting of chloride, hydroxide, sulfate, and mixtures of two or more thereof, wherein more preferably the one or more tetraalkylammonium cation $R^1R^2R^3R^4N^+$-containing compounds and/or that the one or more tetraalkylphosphonium cation $R^1R^2R^3R^4P^+$-containing compounds are hydroxides and/or bromides, and even more preferably bromides.

25. The process of any one of embodiments 22 to 24, wherein the one or more organotemplates comprised in the mixture prepared in (1) is selected from the group consisting of N,N,N,N-tetra($C_1$-$C_4$)alkylammonium and N,N,N,N-tetra($C_1$-$C_4$)alkylphosphonium compounds, preferably from the group consisting of N,N,N,N-tetra($C_1$-$C_3$)alkylammonium and N,N,N,N-tetra ($C_1$-$C_3$)alkylphosphonium compounds, more preferably from the group consisting of N,N,N,N-tetra ($C_1$-$C_2$)alkylammonium and N,N,N,N-tetra($C_1$-$C_2$)alkylphosphonium compounds, more preferably from the group consisting of N,N,N,N-tetra($C_1$-$C_2$)alkylammonium and N,N,N,N-tetra($C_1$-$C_2$)alkylphosphonium compounds, more preferably from the group consisting of N,N,N,N-tetraethylammonium compounds, N,N,N, N-tetramethylammonium compounds, N,N,N,N-tetraethylphosphonium compounds, N,N,N,N-tetramethylphosphonium compounds, and mixtures of two or more thereof, wherein even more preferably the one or more organotemplates comprise one or more N,N,N,N-tetraethylammonium or N,N,N,N-tetraethylphosphonium compounds, preferably one or more N,N,N,N-tetraethylammonium compounds.

26. The process of any of embodiments 22 to 25, wherein the organotemplate:YO$_2$ molar ratio of the one or more organotemplates to YO$_2$ in the mixture provided according to (1) ranges from 0.005 to 0.14, preferably from 0.01 to 0.3, more preferably from 0.02 to 0.2, more preferably from 0.025 to 0.14, more preferably from 0.03 to 0.1, more preferably from 0.035 to 0.08, more preferably from 0.04 to 0.06, and more preferably from 0.045 to 0.055.

27. The process of embodiment 22, wherein the mixture prepared in (1) and crystallized in (2) contains substantially no organotemplates with the exception of organotemplate which may optionally be contained in the micropores of the zeolitic material preferably employed as seed crystals, wherein more preferably the mixture prepared in (1) and crystallized in (2) contains substantially no organotemplates.

28. The process of any of embodiments 22 to 27, wherein the mixture prepared in (1) and crystallized in (2) contains substantially no zeolitic material, wherein preferably the mixture prepared in (1) and crystallized in (2) contains substantially no seed crystals.

29. The process of any of embodiments 22 to 28, wherein in (6) the step of subjecting the zeolitic material to an ion-exchange procedure includes the steps of
   - (6.a) subjecting the zeolitic material obtained in (2), (3), (4), or (5) to an ion-exchange procedure, wherein extra-framework ions contained in the zeolitic material are ion-exchanged against NH$_4^+$;
   - (6.b) calcining the ion-exchanged zeolitic material obtained in (6.a) for obtaining the H-form of the zeolitic material.

30. The process of embodiment 29, wherein calcining in (5), (6.b), (8) and/or (12) is conducted at a temperature in the range of from 200 to 850° C., preferably of from 250 to 800° C., more preferably of from 300 to 750° C., more preferably of from 350 to 700° C., more preferably of from 400 to 650° C., more preferably of from 450 to 620° C., more preferably of from 500 to 600° C., more preferably of from 520 to 580° C., and more preferably of from 540 to 560° C.

31. The process of embodiment 29 or 30, wherein calcining of the zeolitic material in (5), (6.b), (8), and/or (12) is effected by calcining of the zeolitic material for a duration ranging from 0.5 to 36 h, preferably from 1 to 32 h, more preferably from 2 to 28 h, more preferably from 4 to 24 h, more preferably from 6 to 20 h, more preferably from 8 to 18 h, more preferably from 10 to 14 h, and more preferably from 11.5 to 12.5 h.

32. The process of any of embodiments 22 to 31, wherein in (7) the zeolitic material is ion-exchanged such as to obtain a loading of Cu in the zeolitic material ranging from 0.1 to 10 wt.-% calculated as the element and based on 100 wt.-% of YO$_2$ contained in the zeolitic material, preferably from 0.5 to 8 wt.-%, more preferably from 1 to 6 wt.-%, more preferably from 1.2 to 5 wt.-%, more preferably from 1.5 to 4 wt.-%, more preferably from 1.8 to 3.5 wt.-%, more preferably from 2 to 3 wt.-%, more preferably from 2.3 to 2.9 wt.-%, and more preferably from 2.5 to 2.7 wt.-%.

33. The process of any of embodiments 22 to 32, wherein Y is selected from the group consisting of Si, Sn, Ti, Zr, Ge, and combinations of two or more thereof, Y preferably being Si.

34. The process of any of embodiments 22 to 33, wherein the at least one source for YO$_2$ comprises one or more compounds selected from the group consisting of silicas, silicates, and mixtures thereof,
preferably from the group consisting of fumed silica, silica hydrosols, reactive amorphous solid silicas, silica gel, silicic acid, water glass, sodium metasilicate hydrate, sesquisilicate, disilicate, colloidal silica, silicic acid esters, tetraalkoxysilanes, and mixtures of two or more thereof,
more preferably from the group consisting of fumed silica, silica hydrosols, silica gel, silicic acid, water glass, colloidal silica, silicic acid esters, tetraalkoxysilanes, and mixtures of two or more thereof,
more preferably from the group consisting of fumed silica, silica hydrosols, silica gel, colloidal silica, and mixtures of two or more thereof,
more preferably from the group consisting of fumed silica, silica gel, colloidal silica, and mixtures of two or more thereof,
wherein more preferably the at least one source of $YO_2$ is selected from the group consisting of fumed silica, colloidal silica, and mixtures thereof, wherein more preferably fumed silica is employed as the source of $YO_2$.

35. The process of any of embodiments 22 to 34, wherein X is selected from the group consisting of Al, B, In, Ga, and combinations of two or more thereof, X preferably being Al.

36. The process of any of embodiments 22 to 35, wherein the at least one source for $X_2O_3$ comprises one or more aluminum salts, preferably an aluminate of an alkali metal, wherein the alkali metal is preferably selected from the group consisting of Li, Na, K, Rb, and Cs, wherein more preferably the alkali metal is Na and/or K, and wherein even more preferably the alkali metal is Na.

37. The process of any of embodiments 22 to 36, wherein the $YO_2:X_2O_3$ molar ratio of the mixture prepared in (1) ranges from 2 to 50, preferably from 4 to 40, more preferably from 6 to 35, more preferably from 10 to 30, more preferably from 13 to 25, more preferably from 15 to 23, more preferably from 17 to 22, and more preferably from 19 to 21.

38. The process of any of embodiments 22 to 37, wherein the seed crystals comprise a zeolitic material, preferably one or more zeolites, more preferably one or more zeolites having a BEA framework structure, wherein more preferably the seed crystals comprise zeolite beta, and wherein more preferably zeolite beta is employed as the seed crystals for preparing the mixture in (1).

39. The process of any of embodiments 22 to 38, wherein the amount of seed crystals in the mixture prepared in (1) ranges from 0.1 to 15 wt.-% based on 100 wt.-% of $YO_2$ contained in the mixture, preferably from 0.5 to 10 wt.-%, more preferably from 0.8 to 8 wt.-%, more preferably from 1 to 5 wt.-%, more preferably from 1.3 to 3 wt.-%, and more preferably from 1.5 to 2.5 wt.-%.

40. The process of any of embodiments 22 to 39, wherein the mixture prepared in (1) further comprises a solvent system containing one or more solvents, wherein the solvent system preferably comprises one or more solvents selected from the group consisting of polar protic solvents and mixtures thereof,
preferably from the group consisting of n-butanol, isopropanol, propanol, ethanol, methanol, water, and mixtures thereof,
more preferably from the group consisting of ethanol, methanol, water, and mixtures thereof,
wherein more preferably the solvent system comprises water, and wherein more preferably water is used as the solvent system, preferably deionized water.

41. The process of embodiment 40, wherein the mixture prepared in (1) and crystallized in (2) comprises one or more organotemplates, and wherein the mixture prepared in (1) comprises water as the solvent system, wherein the $H_2O:YO_2$ molar ratio of the mixture prepared in (1) preferably ranges from 5 to 70, preferably from 10 to 65, more preferably from 15 to 60, more preferably from 20 to 55, more preferably from 25 to 50, more preferably from 30 to 47, more preferably from 35 to 45, more preferably from 37 to 43, and more preferably from 39 to 41.

42. The process of embodiment 41, wherein the mixture prepared in (1) and crystallized in (2) comprises seed crystals, and wherein the mixture prepared in (1) comprises water as the solvent system, wherein the $H_2O:YO_2$ molar ratio of the mixture prepared in (1) preferably ranges from 5 to 45, preferably from 10 to 40, more preferably from 12 to 35, more preferably from 15 to 30, more preferably from 17 to 27, more preferably from 19 to 25, and more preferably from 21 to 23.

43. The process of any of embodiments 22 to 42, wherein the mixture prepared in (1) further comprises one or more alkali metals (AM), preferably one or more alkali metals selected from the group consisting of Li, Na, K, Cs, and mixtures thereof, wherein more preferably the mixture prepared in (1) further comprises Na and/or K, more preferably Na as the alkali metal AM.

44. The process of embodiment 43, wherein the mixture prepared in (1) and crystallized in (2) comprises one or more organotemplates, and wherein the $AM:YO_2$ molar ratio of alkali metals to $YO_2$ in the mixture prepared in (1) ranges from 0.05 to 2, preferably from 0.1 to 1.5, more preferably from 0.2 to 1, more preferably from 0.3 to 0.7, more preferably from 0.35 to 0.65, more preferably from 0.4 to 0.6, and more preferably from 0.45 to 0.55.

45. The process of embodiment 44, wherein the mixture prepared in (1) and crystallized in (2) comprises seed crystals, and wherein the $AM:YO_2$ molar ratio of alkali metals to $YO_2$ in the mixture prepared in (1) ranges from 0.3 to 2, preferably from 0.5 to 1.5, more preferably from 0.8 to 1.2, more preferably from 1 to 1, more preferably from 1.2 to 0.8, more preferably from 1.3 to 0.5, and more preferably from 1.35 to 1.4.

46. The process of any of embodiments 43 to 45, wherein the $YO_2:X_2O_3:AM$ molar ratio of the mixture prepared in (1) ranges from 1:(0.02-0.5):(0.05-2), preferably from 1:(0.025-0.25):(0.05-2), more preferably from 1:(0.029-0.17):(0.1-1.5), more preferably from 1:(0.033-0.1):(0.2-1), more preferably from 1:(0.04-0.08):(0.3-0.7), more preferably from 1:(0.043-0.7):(0.35-0.65), more preferably from 1:(0.045-0.06):(0.4-0.6), and more preferably from 1:(0.045-0.05):(0.45-0.55).

47. The process of any of embodiments 22 to 46, wherein the crystallization in (2) involves heating of the mixture prepared in (1), preferably to a temperature ranging from 75 to 210° C., more preferably from 100 to 200° C., more preferably from 130 to 190° C., more preferably from 150 to 185° C., more preferably from 160 to 180° C., and more preferably from 165 to 175° C.

48. The process of any of embodiments 22 to 47, wherein the crystallization in (2) is conducted under autogenous pressure, preferably under solvothermal conditions, and more preferably under hydrothermal conditions.
49. The process of any of embodiments 22 to 48, wherein the crystallization in (2) involves heating of the mixture prepared in (1) for a period in the range of from 60 to 120 h, more preferably from 65 to 100 h, more preferably from 70 to 95 h, more preferably from 75 to 90 h, more preferably from 80 to 88 h, and more preferably from 82 to 86 h.
50. The process of any of embodiments 22 to 49, wherein the zeolitic material having an MOR framework structure crystallized in (2) is Mordenite.
51. The process of any of embodiments 22 to 50, wherein the mixture prepared in (1) and crystallized in (2) contains substantially no phosphorous.
52. The process of any of embodiments 22 to 51, wherein the framework of the zeolitic material obtained in (2) contains substantially no phosphorous, wherein preferably the zeolitic material obtained in (2) contains substantially no phosphorous.
53. The process of any of embodiments 22 to 52, wherein the copper ion-exchanged zeolitic material obtained in (7) is not subject to a temperature of 540° C. or greater, more preferably of 520° C. or greater, more preferably of 500° C. or greater, more preferably of 450° C. or greater, more preferably of 400° C. or greater, more preferably of 350° C. or greater, more preferably of 300° C. or greater, more preferably of 250° C. or greater, more preferably of 200° C., and more preferably of 150° C. or greater.
54. The process of any of embodiments 22 to 53, the process further comprising
  (9) mixing the copper ion-exchanged zeolitic material obtained in (7) or (8) with one or more binders;
  (10) kneading of the mixture obtained in (9);
  (11) molding of the kneaded mixture obtained in (10) to obtain one or more moldings; and
  (12) drying and/or calcining the one or more moldings obtained in (11).
55. The process of embodiment 54, wherein the one or more binders are selected from the group consisting of inorganic binders, wherein the one or more binders preferably comprise one or more sources of a metal oxide and/or of a metalloid oxide or one or more sources of graphite, wherein the one or more sources of a metal oxide and/or of a metalloid oxide are preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, and mixtures of two or more thereof, wherein more preferably the one or more binders comprise one or more sources of silica, alumina, zirconia, and/or graphite, the one or more binders preferably comprising one or more sources of silica, alumina, and/or zirconia, wherein more preferably the binder consists of one or more sources silica, alumina, and/or zirconia, preferably of silica, alumina, and/or zirconia.
56. The process of any of embodiments 1 to 55, wherein 2-aminoethanol comprised in the gas stream obtained in (iii) is separated from said gas stream and recycled to (ii).

EXAMPLES

Figure 1:
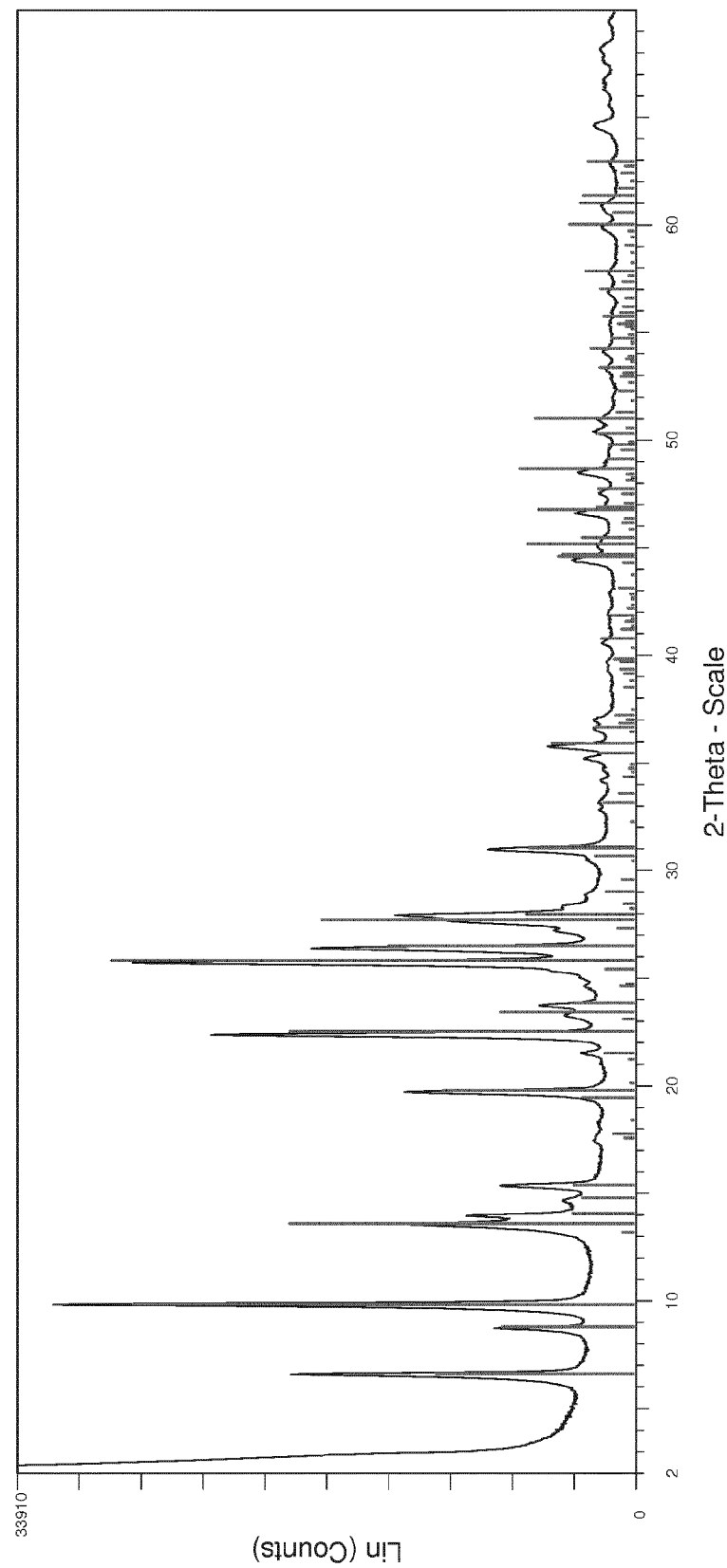
FIG. 1 shows the powder X-ray diffraction pattern of the Na-Mordenite obtained in Example 2, wherein the line pattern of sodium Mordenite from a crystallographic database has been included for comparative purposes. The X-ray diffraction pattern shown in the figure was measured using Cu K alpha-1 radiation. In the respective diffractogram, the diffraction angle 2 theta in ° is shown along the abscissa and the intensities are plotted along the ordinate.

The crystallite size of the samples was determined using X-ray diffraction by fitting the diffracted peak width using the software TOPAS 4.2. Instrumental broadening was considered during the peak fitting using the fundamental parameter approach as described in TOPAS 4.2 Users Manual (Bilker AXS GmbH, Östliche Rheinbrückenstr. 49, 76187 Karlsruhe, Germany). This leads to a separation of the instrumental from the sample broadening. The sample contribution was determined using a single Lorentzian profile function that is defined in the following equation:

$$\beta = \lambda/(L \cdot \cos \theta)$$

where $\beta$ is the Lorentzian full width at half maximum (FWHM), $\lambda$ is the X-ray wavelength of the CuK$\alpha$ radiation used, L is the crystallite size, and $\theta$ is the half the scattering angle of the peak position.

The crystallite size of the 002 reflection in samples having the MOR framework type was determined in a refinement of the local data surrounding the 002 reflection, from 21° to 24.2° (2θ). Single peaks with varying crystallite sizes model the surrounding reflections.

The data was collected in the Bragg-Brentano geometry from 2° to 70° (2θ), using a step size of 0.02° (2θ).

Reference Example 1

Synthesis of H-Mordenite

In a 5 l plastic beaker 120 g fumed silica (CAB-O-SIL M5, Sigma-Aldrich) are suspended in 900 g deionized water. To this suspension a mixture of 52.04 g tetraethylammonium bromide (TEABr, Aldrich) in 161.7 g deionized water is added. The resulting mixture is agitated for 1 h at a stirring speed of 200 rpm. Then, a mixture of 36.5 g sodium hydroxide flakes (NaOH, Sigma-Aldrich) in 161.7 g deionized water is added. The resulting mixture is then agitated for 1.5 h at a stirring speed of 300 rpm. Subsequently, 188.6 g deionized water are added and then a mixture of 15.66 g sodium aluminate (NaAlO$_2$, Sigma-Aldrich) in 188.6 g deionized water. The resulting mixture is then agitated for 1 h at a stirring speed of 200 rpm. The pH value of the mixture was determined to be 12.5. A gel is formed which aged over night.

The synthetic gel displaying a molar composition of 0.28 Na$_2$O:0.048 Al$_2$O$_3$:SiO$_2$:44.5 H$_2$O:0.13 TEABr is then crystallized in a pressure tight vessel for 84 h at 170° C. under agitating at a stirring speed of 250 rpm. Then, the resulting product is filtered off as a solid and washed with deionized water until the electrical conductance of the washing water reaches a value lower than 150 µS. The solids are then dried in air at 90° C. for 12 h. Subsequently, the solids are heated in air to 90° C. with a heating rate of 3.5° C. per minute and then left at said temperature for 2 h. Then the solids are heated to 120° C. with a heating rate of 1.5° C. per minute and then left at said temperature for 2 h. Then the solids are heated to 550° C. with a heating rate of 4.5° C./min and left at said temperature for 12 h. The yield was 66 g.

According to the elemental analysis the resulting product had the following contents determined per 100 g substance of 0.1 g carbon, 5.0 g aluminum, 3.2 g sodium and 37 g silicon.

The BET surface area was determined to be 382 m²/g. The crystallinity of the product was measured to be 86%.

As taken from the X-ray diffraction pattern of the resulting product, the zeolitic material obtained displays the MOR framework structure as the single crystalline phase, wherein the average crystal size along the 002 axis of the crystallites as calculated from the X-ray diffraction data was determined to be 58 nm.

In a 2 liter stirring apparatus, 50 g of ammonium nitrate dissolved in 450 g of distilled water were placed as an aqueous solution (10 wt.-% $NH_4NO_3$), 50 g of the zeolitic material were added, and the resulting mixture was stirred for 2 h at 80° C. The zeolitic material was then filtered off and a new 10-wt.% aqueous solution containing 50 g of ammonium nitrate dissolved in 450 g of distilled water was then placed in the stirring apparatus to which the filtered off zeolitic material was added and the resulting mixture again stirred for 2 h at 80° C. The zeolitic material was then filtered off and washed with distilled water until the wash water was free of nitrate. The washed material was then dried for 5 h at 120° C. and subsequently calcined at 500° C. for 5 h with a heating rate of 2° C./min. The entire procedure was then repeated, affording 43.7 g of the H-form of the zeolitic material.

According to the elemental analysis, the resulting sample had the following contents determined per 100 g substance of <0.1 g carbon, 4.9 g aluminum, 0.06 g sodium and 38 g silicon.

The BET surface area was determined to be 432 m²/g.

Reference Example 2

Synthesis of H-Mordenite

In a 5 l plastic beaker 120 g fumed silica (CAB-O-SIL M5, Sigma-Aldrich) are suspended in 900 g deionized water. To this suspension a mixture of 52.04 g tetraethylammonium bromide (TEABr, Aldrich) in 161.7 g deionized water is added. The resulting mixture is agitated for 1 h at a stirring speed of 200 rpm. Then, a mixture of 36.5 g sodium hydroxide flakes (NaOH, Sigma-Aldrich) in 161.7 g deionized water is added. The resulting mixture is then agitated for 1.5 h at a stirring speed of 300 rpm. Subsequently, 188.6 g deionized water are added and then a mixture of 15.66 g sodium aluminate ($NaAlO_2$, Sigma-Aldrich) in 188.6 g deionized water. The resulting mixture is then agitated for 1 h at a stirring speed of 200 rpm. The pH value of the mixture was determined to be 12.2. A gel is formed which aged over night.

The synthetic gel displaying a molar composition of 0.28 $Na_2O$:0.048 $Al_2O_3$:$SiO_2$:44.5 $H_2O$:0.13 TEABr is then crystallized in a pressure tight vessel for 72 h at 170° C. under agitating at a stirring speed of 250 rpm. Then, the resulting product is filtered off as a solid and washed with deionized water until the electrical conductance of the washing water reaches a value lower than 150 µS. The solids are then dried in air at 90° C. for 12 h. Subsequently, the solids are heated in air to 90° C. with a heating rate of 3.5° C. per minute and then left at said temperature for 2 h. Then the solids are heated to 120° C. with a heating rate of 1.5° C. per minute and then left at said temperature for 2 h. Then the solids are heated to 550° C. with a heating rate of 4.5° C./min and left at said temperature for 12 h. The yield was 82 g.

According to the elemental analysis the resulting product had the following contents determined per 100 g substance of <0.1 g carbon, 4.9 g aluminum, 3.2 g sodium and 37 g silicon.

The BET surface area was determined to be 404 m²/g. The crystallinity of the product was measured to be 90%.

As taken from the X-ray diffraction pattern of the resulting product, the zeolitic material obtained displays the MOR framework structure as the single crystalline phase, wherein the average crystal size as calculated from calculated from the X-ray diffraction data was determined to be 59 nm, and the average crystal size along the 002 axis of the crystallites was determined to be 46 nm.

In a 2 liter stirring apparatus, 70 g of ammonium nitrate dissolved in 630 g of distilled water were placed as an aqueous solution (10 wt.-% $NH_4NO_3$), 70 g of the zeolitic material were added, and the resulting mixture was stirred for 2 h at 80° C. The zeolitic material was then filtered off and washed with distilled water until the wash water was free of nitrate. The filtrate was discarded and a new 10-wt.% aqueous solution containing 70 g of ammonium nitrate dissolved in 630 g of distilled water was then placed in the stirring apparatus to which the washed zeolitic material was added and the resulting mixture again stirred for 2 h at 80° C. The zeolitic material was then filtered off and washed anew with distilled water until the wash water was free of nitrate. The washed material was then dried for 5 h at 120° C. and subsequently calcined at 500° C. for 5 h with a heating rate of 2° C./min. The entire procedure was then repeated, affording 63.4 g of the H-form of the zeolitic material.

According to the elemental analysis, the resulting sample had the following contents determined per 100 g substance of <0.1 g carbon, 5.0 g aluminum, 0.01 g sodium and 38 g silicon.

The BET surface area was determined to be 474 m²/g.

Example 1

Synthesis of Copper-Exchanged Mordenite 1.5 liters of a 0.01 molar aqueous solution of copper(II) acetate (3 grams in 1.5 liters) were placed in a 2 liter stirring apparatus and 25 g of the product from Reference Example 2 were then added and the mixture stirred at room temperature for 20 h. The zeolitic material was then filtered off, and the filtrate was discarded. A new solution of 1.5 liters of a 0.01 molar aqueous solution of copper(II) acetate (3 grams in 1.5 liters) was then placed in the 2 liter stirring apparatus and the zeolitic material was added thereto and the mixture stirred at room temperature for 20 h. The zeolitic material was then filtered off, the filtrate discarded, and the zeolitic material was again added to a new solution of 1.5 liters of a 0.01 molar aqueous solution of copper(II) acetate (3 grams in 1.5 liters) and stirred for 20 h at room temperature. The resulting product was then separated from the solution by centrifugation, the solution discarded, and the zeolitic material subsequently suspended in 1.25 liters of distilled water. The zeolitic material was then separated from the solution by centrifugation, the washwater was discarded, and the washing procedure with distilled water was repeated 3 times for washing the zeolitic material. The zeolitic material was then dried for 24 h at 110° C., thus affording 24.4 g of a copper-exchanged zeolitic material.

According to the elemental analysis the resulting product had the following contents determined per 100 g substance of <0.1 g carbon, 4.8 g aluminum, 2.6 g copper and 35 g silicon.

The BET surface area was determined to be 371 $m^2$/g.

Example 2

Synthesis of Copper-Exchanged Mordenite

In a stirring apparatus, 2.4 kg fumed silica (CAB-O-SIL M5, Sigma-Aldrich) are suspended in 18 kg deionized water. To this suspension an solution of 1.04 kg tetraethylammonium bromide (TEABr, Aldrich) in 1.04 kg deionized water is added. The resulting mixture is agitated for 1 h at a stirring speed of 150 rpm. Then, a solution of 0.73 kg sodium hydroxide flakes (NaOH, Sigma-Aldrich) in 3.5 kg deionized water is added. The resulting mixture is then agitated for 1.5 h at a stirring speed of 180 rpm. Subsequently, a solution of 0.31 kg sodium aluminate ($NaAlO_2$, Sigma-Aldrich) in 4 kg deionized water are added, together with 3 kg of deionized water with which the receptacle containing the previous solution was washed out. The resulting mixture is then agitated for 1 h at a stirring speed of 180 rpm. The pH value of the resulting gel was determined to be 13.1. The gel was then aged over night.

The synthetic gel displaying a molar composition of 0.5 $Na_2O$:0.0475 $Al_2O_3$:$SiO_2$:44.5 $H_2O$:0.125 TEABr is then heated under stirring at 200 rpm to 170° C. in a pressure tight vessel and held at that temperature for 84 h under further stirring at the same speed. Then, the resulting product displaying a pH of 12.5 is filtered off as a solid and washed five times with 50 liters of deionized water, respectively, until the electrical conductance of the washing water reaches a value of 85 µS. The filter cake is then heated to 100° C. and a nitrogen stream is conducted over the filter cake for 16 h for drying at that temperature. 1.667 kg of a crystalline material was thus obtained, which is then calcined for 12 h at 550° C., thus obtaining 1.533 kg of a white powder.

According to the elemental analysis the resulting product had the following contents determined per 100 g substance of <0.1 g carbon, 5.3 g aluminum, 3.2 g sodium and 35 g silicon.

The BET surface area was determined to be 400 $m^2$/g. The crystallinity of the product was measured to be 93%.

As taken from the X-ray diffraction pattern of the resulting product displayed in FIG. 1, the zeolitic material obtained displays the MOR framework structure as the single crystalline phase. The average crystal size of the crystallites as calculated from the X-ray diffraction data was determined to be 57.5 nm.

325 g of distilled water were placed in a stirring apparatus and 50 g of the crystallization product having the MOR type framework structure were then added and the heated to 60° C. 7.15 g of copper(II) acetate and a solution of 0.39 g acetic acid in 0.17 g distilled water (70% acetic acid solution) were then added to the mixture which was then stirred at 60° C. for 1 h. 243.75 g of distilled water (having room temperature) were then added to the hot mixture, after which the zeolitic material was immediately filtered off. The filter cake was then dried for 12 h at 110° C. and subsequently heated to 500° C. using a heating ramp of 2° C./min and calcined at that temperature for 5 h, thus affording 51.5 g of a copper-exchanged zeolitic material.

According to the elemental analysis the resulting product had the following contents determined per 100 g substance of <0.1 g carbon, 4.7 g aluminum, 0.08 g copper, 0.07 g Na, and 35 g silicon.

The BET surface area was determined to be 377 $m^2$/g.

Example 3

Synthesis of Copper-Exchanged Mordenite

In a stirring apparatus, 650 g of ammonium nitrate were placed as a solution in 5.85 kg of distilled water (10 wt.-% $NH_4NO_3$), 650 g of the non copper ion-exchanged zeolitic material having the MOR framework structure as obtained from crystallization and after washing, drying and calcining in Example 2 were added to the solution, and the resulting mixture was heated to 80° C. under stirring and held at that temperature for 2 h. The zeolitic material was then filtered off, the filtrate was discarded, and a new 10-wt.% aqueous solution containing 650 g of ammonium nitrate was then placed in the stirring apparatus to which the filtered-off zeolitic material was added and the resulting mixture again stirred for 2 h at 80° C. The zeolitic material was then filtered off and washed with 12 liters of distilled water. The washed material was then dried for 5 h at 120° C. and subsequently calcined at 500° C. for 5 h to afford 1.196 kg of a white powder.

According to the elemental analysis, the resulting sample had the following contents determined per 100 g substance of <0.1 g carbon, 5.4 g aluminum, 0.1 g sodium and 40 g silicon.

A new 10-wt.% aqueous solution containing 650 g of ammonium nitrate was then placed in the stirring apparatus, and the calcined powder was added to the solution, after which the resulting mixture was heated to 80° C. under stirring and held at that temperature for 2 h. The zeolitic material was then filtered off and washed with 12 liters of distilled water. The washed material was then dried for 5 h at 120° C. and subsequently calcined at 500° C. for 5 h to afford 1.172 kg of the H-form of the zeolitic material.

According to the elemental analysis, the resulting sample had the following contents determined per 100 g substance of 4.6 g aluminum, 0.01 g sodium and 38 g silicon.

According to the elemental analysis, the resulting sample had the following contents determined per 100 g substance of <0.1 g carbon, 5.0 g aluminum, 0.01 g sodium and 38 g silicon.

The BET surface area was determined to be 438 $m^2$/g.

1.8 liters of a 0.01 molar aqueous solution of copper(II) acetate (3.6 grams in 1.8 liters) were placed in a 2 liter stirring apparatus and 30 g of the H-form of the zeolitic material were then added and the mixture stirred at room temperature for 20 h. The zeolitic material was then filtered off, and the filtrate was discarded. A new solution of 1.8 liters of a 0.01 molar aqueous solution of copper(II) acetate (3.6 grams in 1.8 liters) was then placed in the 2 liter stirring apparatus and the zeolitic material was added thereto and the mixture stirred at room temperature for 20 h. The zeolitic material was then filtered off, the filtrate discarded, and the zeolitic material was again added to a new solution of 1.8 liters of a 0.01 molar aqueous solution of copper(II) acetate (3.6 grams in 1.8 liters) and stirred for 20 h at room temperature. The resulting product was then separated from the solution by centrifugation, the solution discarded, and the zeolitic material subsequently suspended in 1.5 liters of distilled water. The zeolitic material was then separated from the solution by centrifugation, the washwater was discarded, and the washing procedure with distilled water was repeated 3 times for washing the zeolitic material. The zeolitic material was then dried for 24 h at 110° C., thus affording 22 g of a copper-exchanged zeolitic material.

According to the elemental analysis the resulting product had the following contents determined per 100 g substance of 0.17 g carbon, 4.4 g aluminum, 2.6 g copper and 36 g silicon.

The BET surface area was determined to be 425 m$^2$/g.

Example 4

Synthesis of Copper-Exchanged Mordenite 50 g of the H-form of the zeolitic material obtained in Example 3 which has not been subject to copper ion exchange were placed in a beaker and an aqueous solution of 4.03 copper(II) acetate monohydrate dissolved in 50 ml of distilled water were added thereto and the resulting mixture stirred with a spatula. The zeolitic material was then filtered off and the filter cake was dried in a drying oven at 110° C. for 12 h, and subsequently heated at a rate of 2° C./min to 500° C. and calcined at that temperature for 5 h, thus affording 49 g of a copper ion-exchanged zeolitic material.

According to the elemental analysis the resulting product had the following contents determined per 100 g substance of <0.1 g carbon, 4.7 g aluminum, 2.6 g copper and 38 g silicon.

The BET surface area was determined to be 444 m$^2$/g.

Example 5

Synthesis of Copper-Exchanged Mordenite 325 g of distilled water were placed in a round bottom flask and 50 g of the H-form of the zeolitic material obtained in Example 3 which has not been subject to copper ion exchange is added thereto under stirring, after which the mixture is then heated under stirring to 60° C. 7.15 g of copper(II) acetate and a solution of 0.39 g acetic acid in 0.17 g distilled water (70% acetic acid solution) were then added to the mixture which was then stirred at 60° C. for 1 h. 243.75 g of distilled water (having room temperature) were then added to the hot mixture for cooling, after which the zeolitic material was filtered off. The filter cake was then washed twice with 600 ml of distilled water to obtain a value of 10 µS in the filtrate. The filter cake was then dried for 12 h at 110° C. and subsequently heated to 500° C. using a heating ramp of 2° C./min and calcined at that temperature for 5 h, thus affording 49.5 g of a copper-exchanged zeolitic material.

According to the elemental analysis the resulting product had the following contents determined per 100 g substance of 4.4 g aluminum, 1.9 g copper, and 37 g silicon.

The BET surface area was determined to be 477 m$^2$/g.

Example 6

Catalyst Testing

Into a carrier gas stream consisting of nitrogen and specific amounts of methane (as internal standard), hydrogen, ammonia, and monoethanolamine (MEOA) are evaporated at a temperature according to their partial pressures. Ammonia is evaporated in a first evaporator whereas MEOA is evaporated in a second evaporator downstream. Afterwards the resultant gas vapor stream is heated to 200° C.

The zeolitic materials to be tested were respectively admixed with 3 wt.-% graphite and homogenized by shaking and mixing, if necessary using a mortar and pestle. The homogenized mixture is then pelletized using a 13 mm diameter pelletizing tool set applying 10-40 kN of force depending on the zeolite in order to obtain stable pellets and thus a stable target fraction, wherein the pellets obtained are 2-3 mm in height and have a diameter of 13 mm. The pellets thus obtained were then precrushed with mortar and pestle and sieved through a 1000 µm analytical sieve. Crushing and sieving was repeated for obtaining the desired target fraction having a particle diameter in the range of from 315-500 µm using suitable analytical sieves and a pestle, and wherein the fines (<315 µm) were removed by sieving on a sieving tool (e.g. Retsch AS 200) or by sieving manually.

This gas vapor stream is fed to a reactor filled with 1 cm$^3$ of catalyst particles that are of the size in the range of 315-500 µm. The catalyst bed has a diameter of 4 mm and a length of 80 mm. Due to the low diameter of the catalyst bed it is isothermal. Before the catalyst bed the gas vapor stream is heated to the reaction temperature by passing it through an inert bed. Both the catalyst bed and the inert bed are heated externally to the reaction temperature. Downstream to the catalyst bed the product stream is diluted and cooled to 250° C. Further downstream its composition is measured by an online-GC.

Results were calculated by referencing the ratio of educt to internal standard (IS) to the same ratio as obtained by analyzing the gas vapor stream from a by-pass tubing. Thus undetected products (high-boilers, coke) are taken into account as well. The following formulas give the detailed procedure:

Conversion: $X(\text{educt})=1-c(\text{educt})/c(\text{IS})/(c(\text{educt\_by-pass})/c(\text{IS-by-pass}))$ Yields: $Y(\text{product})=c(\text{product})/c(\text{IS})/(c(\text{educt\_by-pass})/c(\text{IS-by-pass}))$ Selectivities: $S(\text{product})=Y(\text{product})/X(\text{educt})$ For the standard experiment the following testing conditions were chosen: gas hourly space velocity (GHSV) of 5000 h$^{-1}$ with MEOA-concentration of 1 vol-%. Apart from the main educt MEOA the gas stream consisted of 40 vol.-% ammonia, 20 vol.-% hydrogen and 1 vol.-% methane as internal standard with nitrogen as balance. The catalysts were heated in nitrogen to the reaction temperature of 300° C. and then the gas feed was switched to testing conditions. The results obtained from catalytic testing performed on Examples 1-5 and Reference Examples 1 and 2 are displayed in Table 1 below, wherein the yield of ethylene diamine and the conversion rate of MEOA are respectively shown in %, as well as the amounts of diethylenetriamine (DETA), aminoethylethanolamine (AEEA), piperazine (PIP), 1-(2-aminoethyl)piperazine (AE-PIP), and 1,4-diazabicyclo[2.2.2]octane (DABCO) generated in the reaction in %. As regards the results obtained for Example 1 and Reference Example 2, values are indicated from 2 different runs, respectively.

TABLE 1

Results from catalytic testing of Examples 1-5 and Reference Examples 1 and 2.

| Example | Cu [wt.-%] | EDA Yield [%] | DETA Yield [%] | AEEA Yield [%] | PIP Yield [%] | AE-PIP Yield [%] | DABCO Yield [%] | MEOA conversion [%] |
|---|---|---|---|---|---|---|---|---|
| Ex. 1 | 2.6 | 35.2 | 0.7 | 1.8 | 1.7 | 2.8 | 1.5 | 52.5 |
| Ref. Ex. 2 | — | 31.6 | 0.6 | 1.9 | 1.9 | 3.3 | 2.0 | 51.0 |
| Ex. 5 | 1.9 | 27.1 | 0.2 | 2.0 | 1.3 | 2.2 | 1.0 | 42.2 |
| Ex. 3 | 2.6 | 35.9 | 0.8 | 1.8 | 2.1 | 3.1 | 1.9 | 58.9 |
| Ex. 4 | 2.6 | 25.0 | 0.2 | 1.7 | 1.2 | 2.1 | 0.9 | 39.5 |
| Ref. Ex. 1 | — | 20.8 | <0.1 | 2.4 | 0.7 | 1.4 | 0.8 | 34.3 |
| Ex. 2 | 0.08 | 9.4 | <0.1 | 1.6 | 0.7 | 1.3 | 0.7 | 20.3 |

Thus, as may be taken from the results displayed in Table 1, all of the inventive samples display a superior performance in the catalytic amination of MEOA to EDA when the zeolitic material of the reference examples having the MOR framework structure are ion exchanged with copper. Thus, said effect may be observed when comparing the results obtained for reference example 2 compared to the results for example 1 after having subjected a sample from reference example 2 to ion exchange. Same applies accordingly when comparing the results obtained for reference example 1 compared to the results for examples 3, 4, and 5 after having respectively subjected samples as obtained according to reference example 1 to ion exchange with copper.

As regards the results of obtained for example 2, these may not be directly compared to the other examples and reference examples which were all obtained using the H-form of the zeolitic materials having the MOR framework structure, respectively. In particular, it is noted that example to was obtained from the sodium-form of a zeolitic material having the MOR framework structure, which was subsequently subject to partial ion exchange of the sodium ions against copper (II) ions. Consequently, a comparison of the sample from example 2 would necessarily require that a sample of the zeolitic material containing the same amount of sodium yet which has not been ion exchanged with copper be tested in the catalytic amination of MEOA.

Therefore, as demonstrated in the foregoing, it has surprisingly been found that a zeolitic material having the MOR framework structure and which has been ion exchanged with copper not only displays a considerably improved catalytic activity in the amination of MEOA, but furthermore displays a highly improved selectivity as may be observed from the results for the yield in EDA achieved by the inventive samples. Consequently, it has quite unexpectedly been found that a highly improved process for the amination of MEOA to EDA may be obtained by using a copper ion exchanged zeolitic material having the MOR framework structure.

LIST OF THE CITED PRIOR ART REFERENCES

WO 2014/135662 A
U.S. Pat. No. 7,605,295
U.S. Pat. No. 7,687,423 B2
Grundner, Sebastian et al. in Nat. Commun. 2015, Vol. 6article number 7546
U.S. Pat. No. 4,918,233
CN 1962058 A
JP H0687797 A
JP H07247245 A
CN 101215239 B
CN 101406845 A
CN 102974393 A
CN 103007984 A
CN102233272A
CN102190588A
inaugural thesis "Heterogeneous Transition Metal Catalyzed Amination of Aliphatic Diols" from Achim Fischer, Diss. ETH No 12978, 1998
WO 2009/083580 A1
U.S. Pat. No. 4,918,233
CN 101215239 A
DE 10 2005 047464 A1

The invention claimed is:

1. A process for the conversion of 2-aminoethanol to ethane-1,2-diamine and/or linear polyethylenimines of the formula $H_2N-[CH_2CH_2NH]_n-CH_2CH_2NH_2$ wherein $n \geq 1$ comprising
   (i) providing a catalyst comprising a zeolitic material having the MOR framework structure comprising $YO_2$ and $X_2O_3$, wherein Y is Si and X is Al, said zeolitic material containing copper as extra-framework ions;
   (ii) providing a gas stream comprising 2-aminoethanol and ammonia;
   (iii) contacting the catalyst provided in (i) with the gas stream provided in (ii) for converting 2-aminoethanol to ethane-1,2-diamine and/or linear polyethylenimines,
   wherein the zeolitic material having the MOR framework structure is prepared by a process comprising
   (1) preparing a mixture comprising at least one source of $YO_2$, at least one source of $X_2O_3$, and comprising one or more organotemplates as structure directing agent and/or comprising seed crystals;
   (2) crystallizing the mixture prepared in (i) for obtaining a zeolitic material having the MOR framework structure; and
   (7) subjecting the zeolitic material obtained in (2) to an ion-exchange procedure, wherein extra-framework ions contained in the zeolitic material are ion-exchanged against $Cu^{2+}$ and/or $Cu^+$.

2. The process of claim 1, wherein the gas stream provided in (ii) and contacted with the catalyst in (iii) contains 2-aminoethanol in an amount in the range of from 0.1 to 10 vol.-%.

3. The process of claim 1, wherein the gas stream provided in (ii) and contacted with the catalyst in (iii) contains ammonia in an amount in the range of from 5 to 90 vol.-%.

4. The process of claim 1, wherein the gas stream provided in (ii) and contacted with the catalyst in (iii) contains 1 vol.-% or less of hydrogen.

5. The process of claim 1, wherein the gas stream provided in (ii) and contacted with the catalyst in (iii) further contains hydrogen in an amount in the range of from 0.1 to 70 vol.-%.

6. The process of claim 1, wherein the gas stream provided in (ii) and contacted with the catalyst in (iii) contains $H_2O$ in an amount of 5 vol.-% or less.

7. The process of claim 1, wherein the gas stream provided in (ii) is heated to a temperature in the range of from 120 to 600° C., prior to contacting with the catalyst in (iii) at that temperature.

8. The process of claim 1, wherein the zeolitic material contains from 0.5 to 15 wt.-% of copper as extra-framework ions calculated as the element and based on 100 wt-% of $YO_2$ contained in the zeolitic material having the MOR framework structure.

9. The process of claim 1, wherein the $Cu:X_2O_3$ molar ratio of the zeolitic material is in the range of from 0.01 to 2.

10. The process of claim 1, wherein the zeolitic material contains substantially no Na.

11. The process of claim 1, wherein the zeolitic material having the MOR framework structure is prepared by a process further comprising
 (3) isolating the zeolitic material obtained in (2);
 (4) optionally washing the zeolitic material obtained in (2) or (3);
 (5) optionally drying and/or calcining the zeolitic material obtained in (2), (3), or (4);
 (6) optionally subjecting the zeolitic material obtained in (2), (3), (4), or (5) to an ion-exchange procedure, wherein extra-framework ions contained in the zeolitic material are ion-exchanged against $H^+$;
 (7) subjecting the zeolitic material obtained in (3), (4), (5), or (6) to an ion-exchange procedure, wherein extra-framework ions contained in the zeolitic material are ion-exchanged against $Cu^{2+}$ and/or $Cu^+$;
 (8) optionally drying and/or calcining the zeolitic material obtained in (7).

12. The process of claim 11, wherein in (6) the step of subjecting the zeolitic material to an ion-exchange procedure includes the steps of
 (6.a) subjecting the zeolitic material obtained in (2), (3), (4), or (5) to an ion-exchange procedure, wherein extra-framework ions contained in the zeolitic material are ion-exchanged against $NH_4^+$;
 (6.b) calcining the ion-exchanged zeolitic material obtained in (6.a) for obtaining the H-form of the zeolitic material.

13. The process of claim 1, wherein 2-aminoethanol comprised in the gas stream obtained in (iii) is separated from said gas stream and recycled to (ii).

* * * * *